US008829216B2

(12) United States Patent
Forest et al.

(10) Patent No.: US 8,829,216 B2
(45) Date of Patent: Sep. 9, 2014

(54) HYDROXY ESTOLIDES, POLY-CAPPED ESTOLIDES, AND METHODS OF MAKING THE SAME

(75) Inventors: Jeremy Forest, Irvine, CA (US); Travis Thompson, Anaheim, CA (US); Jakob Bredsguard, Lake Forest, CA (US)

(73) Assignee: Biosynthetic Technologies, LLC, Irvine, CA (US)

( * ) Notice: Subject to any disclaimer, the term of this patent is extended or adjusted under 35 U.S.C. 154(b) by 274 days.

(21) Appl. No.: 13/600,704

(22) Filed: Aug. 31, 2012

(65) Prior Publication Data

US 2013/0053589 A1 Feb. 28, 2013

Related U.S. Application Data

(60) Provisional application No. 61/529,884, filed on Aug. 31, 2011, provisional application No. 61/583,139, filed on Jan. 4, 2012.

(51) Int. Cl.
*C07C 51/00* (2006.01)
*C08G 63/20* (2006.01)
*C07D 301/27* (2006.01)
*C07D 493/00* (2006.01)
*C11C 3/00* (2006.01)
*C10M 105/42* (2006.01)
*C07C 69/708* (2006.01)

(52) U.S. Cl.
CPC .......... *C10M 105/42* (2013.01); *C10N 2230/60* (2013.01); *C11C 3/003* (2013.01); *C10N 2220/022* (2013.01); *C10N 2220/023* (2013.01); *C10N 2230/02* (2013.01); *C10N 2220/027* (2013.01); *C07C 69/708* (2013.01); *C10M 2207/301* (2013.01); *C10N 2220/028* (2013.01); *C10N 2220/10* (2013.01); *C11C 3/00* (2013.01)
USPC ........... 554/148; 554/122; 554/149; 524/311; 549/90; 549/515

(58) Field of Classification Search
USPC ............. 554/122, 148, 149; 524/311; 549/90, 549/515
See application file for complete search history.

(56) References Cited

U.S. PATENT DOCUMENTS

| | | | |
|---|---|---|---|
| 5,703,022 A | 12/1997 | Floyd | |
| 6,018,063 A | 1/2000 | Isbell et al. | |
| 6,316,649 B1 | 11/2001 | Cermak et al. | |
| 6,797,753 B2 | 9/2004 | Benecke et al. | |
| 8,236,194 B1 | 8/2012 | Bredsguard et al. | |
| 8,258,236 B2 | 9/2012 | Sawasato et al. | |
| 8,268,199 B1 | 9/2012 | Forest et al. | |
| 8,287,754 B1 | 10/2012 | Bredsguard et al. | |
| 2006/0020062 A1 | 1/2006 | Bloom | |
| 2009/0005508 A1 | 1/2009 | Bloom | |
| 2010/0120643 A1 | 5/2010 | Brown et al. | |
| 2012/0083435 A1 | 4/2012 | Bredsguard | |
| 2012/0172609 A1 | 7/2012 | Bredsguard et al. | |
| 2012/0178660 A1 | 7/2012 | Bredsguard | |

FOREIGN PATENT DOCUMENTS

| | | |
|---|---|---|
| DE | 3203491 A1 | 8/1983 |
| GB | 723244 | 2/1955 |
| WO | WO 01/53247 A1 | 7/2001 |
| WO | WO 2005/030823 A2 | 4/2005 |
| WO | WO-2010/104609 A2 | 9/2010 |

OTHER PUBLICATIONS

Cermak et al., "Synthesis and Physical Properties of Tallow-Oleic Estolide 2-Ethylhexyl Esters," *J. Amer. Oil Chem. Soc.*, 84(5): 449-56 (2007).
International Search Report and Written Opinion for co-pending application PCT/US2012/053316, mailed Nov. 2, 2012.
International Search Report and Written Opinion for counterpart application PCT/US2012/024260, mailed Apr. 26, 2012.
Co-Pending U.S. Appl. No. 13/411,331, filed Mar. 2, 2012.
Notice of Allowance dated Jul. 16, 2012, for U.S. Appl. No. 13/411,331, filed Mar. 2, 2012.
Co-Pending U.S. Appl. No. 13/766,138, filed Feb. 13, 2013.
Gast et al., "Synthetic Lubricants from Polyhydroxystearic Acids," *Indus. and Eng. Chem.*, 46(10): 2205-08 (1954).

*Primary Examiner* — Deborah D Carr
(74) *Attorney, Agent, or Firm* — Jeremy Forest

(57) ABSTRACT

Provided herein are poly-capped estolides, including those of the Formula IV

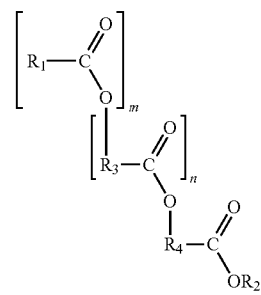

in which n is an integer equal to or greater than 0; m is an integer equal to or greater than 2; $R_1$ is selected from optionally substituted alkyl that is saturated or unsaturated, and branched or unbranched; $R_2$ is selected from hydrogen and optionally substituted alkyl that is saturated or unsaturated, and branched or unbranched; and $R_3$ and $R_4$, independently for each occurrence, are selected from optionally substituted alkyl that is saturated or unsaturated, and branched or unbranched. Hydroxy estolides are also described herein, which may be suitable end products, or serve as intermediates to provide poly-capped estolides. Also provided are compositions containing poly-capped estolides and methods of making both said poly-capped estolides and compositions thereof.

37 Claims, No Drawings

HYDROXY ESTOLIDES, POLY-CAPPED ESTOLIDES, AND METHODS OF MAKING THE SAME

CROSS-REFERENCE TO RELATED APPLICATIONS

This application claims the benefit under 35 U.S.C. §119 (e) of U.S. Provisional Patent Application No. 61/529,884, filed Aug. 31, 2011, and U.S. Provisional Patent Application No. 61/583,139, filed Jan. 4, 2012, both of which are incorporated herein by reference in their entireties for all purposes.

FIELD

The present disclosure relates to base oil stocks and lubricants and methods of making the same. The hydroxy estolides and poly-capped estolides described herein may be suitable for use as biodegradable base oil stocks and lubricants, or intermediates thereof.

BACKGROUND

A variety of commercial uses for fatty esters such as triglycerides have been described. When used as a lubricant, for example, fatty esters can provide a biodegradable alternative to petroleum-based lubricants. However, naturally-occurring fatty esters are typically deficient in one or more areas, including hydrolytic stability and/or oxidative stability.

SUMMARY

Described herein are estolide compounds, estolide-containing compositions, and methods of making the same. In certain embodiments, such compounds and/or compositions may be useful as base oils and lubricants. In certain embodiments, the estolides comprise at least one compound selected from Formula I:

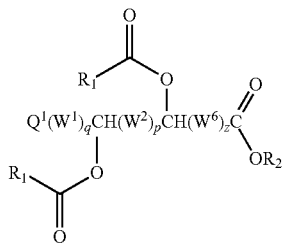

Formula I wherein
z is an integer selected from 0, 1, 2, 3, 4, 5, 6, 7, 8, 9, 10, 11, 12, 13, 14 and 15;
p is an integer selected from 0, 1, 2, 3, 4, 5, 6, 7, 8, 9, 10, 11, 12, 13, 14 and 15;
q is an integer selected from 0, 1, 2, 3, 4, 5, 6, 7, 8, 9, 10, 11, 12, 13, 14 and 15;
$R_1$, independently for each occurrence, is an optionally substituted alkyl that is saturated or unsaturated, and branched or unbranched; and
$R_2$ is selected from hydrogen, optionally substituted alkyl that is saturated or unsaturated, and branched or unbranched, and a substituent represented by Formula II:

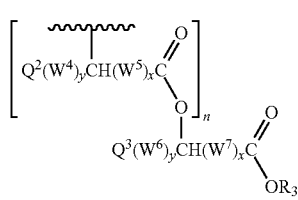

Formula II wherein
x is, independently for each occurrence, an integer selected from 0, 1, 2, 3, 4, 5, 6, 7, 8, 9, 10, 11, 12, 13, 14, 15, 16, 17, 18, 19, and 20;
y is, independently for each occurrence, an integer selected from 0, 1, 2, 3, 4, 5, 6, 7, 8, 9, 10, 11, 12, 13, 14, 15, 16, 17, 18, 19, and 20;
n is 0 or greater than 0;
$R_3$ is selected from hydrogen and optionally substituted alkyl that is saturated or unsaturated, and branched or unbranched;
$W^1$, $W^2$, $W^3$, $W^4$, $W^5$, $W^6$, and $W^7$, independently for each occurrence, are selected from —$CH_2$— and —CH=CH—; and
$Q^1$, $Q^2$, and $Q^3$, independently for each occurrence, are selected from hydrogen and —$CH_3$,
wherein each fatty acid chain residue of said at least one compound is independently optionally substituted.

In certain embodiments, the at least one compound of Formula I is selected from compounds represented by Formula III:

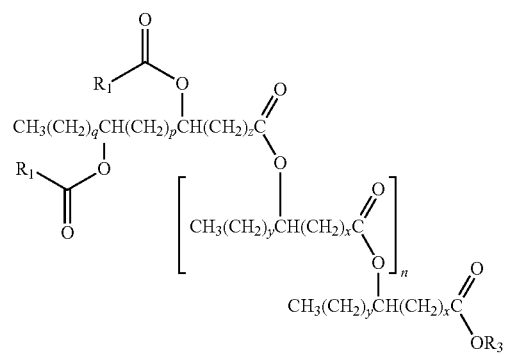

Formula III wherein
x is, independently for each occurrence, an integer selected from 1, 2, 3, 4, 5, 6, 7, 8, 9 and 10;
y is, independently for each occurrence, an integer selected from 1, 2, 3, 4, 5, 6, 7, 8, 9 and 10; and
n is an integer selected from 0, 1, 2, 3, 4, 5, 6, 7 and 8.

In certain embodiments, the estolides comprise at least one compound selected from Formula IV:

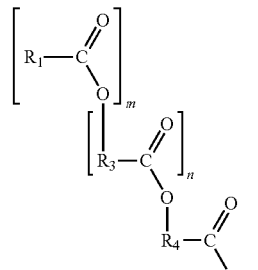

Formula IV wherein
n is equal to or greater than 0;
m is equal to or greater than 2;
$R_2$ is selected from hydrogen and optionally substituted alkyl that is saturated or unsaturated, and branched or unbranched; and $R_1$, $R_3$ and $R_4$, independently for each occurrence, are selected from optionally substituted alkyl that is saturated or unsaturated, and branched or unbranched.

In certain embodiments, the estolides comprise at least one compound selected from Formula V:

$$Q^1(W^1)_q CH_2(W^2)_p CH_2(W^6)_z C \begin{pmatrix} O \\ \| \\ O \\ | \\ \left[ Q^2(W^4)_y CH(W^5)_x C \begin{pmatrix} O \\ \| \\ O \end{pmatrix} \right]_n \\ Q^3(W^6)_y CH(W^7)_x C \begin{pmatrix} O \\ \| \\ OR_2 \end{pmatrix} \end{pmatrix} \qquad \text{Formula V}$$

wherein
$W^1$, $W^2$, $W^3$, $W^4$, $W^5$, $W^6$, and $W^7$, independently for each occurrence, are selected from —$CH_2$—, —CH=CH—, and

[cyclopropane structure with T]

provided that at least one of $W^1$, $W^2$, $W^3$, $W^4$, $W^5$, $W^6$, or $W^7$ is

[cyclopropane structure with T];

T is O;
$Q^1$, $Q^2$, and $Q^3$, independently for each occurrence, are selected from hydrogen and —$CH_3$;
z is an integer selected from 0 to 15;
p is an integer selected from 0 to 15;
q is an integer selected from 0 to 15;
x is, independently for each occurrence, an integer selected from 0 to 20;
y is, independently for each occurrence, an integer selected from 0 to 20;
n is equal to or greater than 0; and
$R_2$ is selected from hydrogen and optionally substituted alkyl that is saturated or unsaturated, and branched or unbranched,
wherein each fatty acid chain residue of said at least one compound is independently optionally substituted.

In certain embodiments, the estolides comprise at least one compound selected from Formula VI:

$$Q^1(W^1)_q \overset{OR_5}{\underset{|}{CH}}(W^2)_p \overset{OR_6}{\underset{|}{CH}}(W^3)_z C \begin{pmatrix} O \\ \| \\ OR_2 \end{pmatrix} \qquad \text{Formula VI}$$

wherein
z is an integer selected from 0, 1, 2, 3, 4, 5, 6, 7, 8, 9, 10, 11, 12, 13, 14 and 15;

p is an integer selected from 0, 1, 2, 3, 4, 5, 6, 7, 8, 9, 10, 11, 12, 13, 14 and 15;
q is an integer selected from 0, 1, 2, 3, 4, 5, 6, 7, 8, 9, 10, 11, 12, 13, 14 and 15;
$R_5$ and $R_6$ are independently selected from hydrogen, —C(O)$R_1$, and an optionally substituted alkyl that is saturated or unsaturated, and branched or unbranched;
$R_1$ is and optionally substituted alkyl that is saturated or unsaturated, and branched or unbranched; and
$R_2$ is selected from hydrogen, optionally substituted alkyl that is saturated or unsaturated, and branched or unbranched, and a substituent represented by Formula II:

$$\left[ Q^2(W^4)_y CH(W^5)_x C \begin{pmatrix} O \\ \| \\ O \end{pmatrix} \right]_n Q^3(W^6)_y CH(W^7)_x C \begin{pmatrix} O \\ \| \\ OR_3 \end{pmatrix} \qquad \text{Formula II}$$

wherein
x is, independently for each occurrence, an integer selected from 0, 1, 2, 3, 4, 5, 6, 7, 8, 9, 10, 11, 12, 13, 14, 15, 16, 17, 18, 19, and 20;
y is, independently for each occurrence, an integer selected from 0, 1, 2, 3, 4, 5, 6, 7, 8, 9, 10, 11, 12, 13, 14, 15, 16, 17, 18, 19, and 20;
n is 0 or greater than 0;
$R_3$ is selected from hydrogen and optionally substituted alkyl that is saturated or unsaturated, and branched or unbranched;
$W^1$, $W^2$, $W^3$, $W^4$, $W^5$, $W^6$, and $W^7$, independently for each occurrence, are selected from —$CH_2$— and —CH=CH—; and
$Q^1$, $Q^2$, and $Q^3$, independently for each occurrence, are selected from hydrogen and —$CH_3$,
wherein each fatty acid chain residue of said at least one compound is independently optionally substituted.

In certain embodiments, the estolides comprise at least one compound of Formula VII:

$$\left[ R_1 - C \begin{pmatrix} O \\ \| \\ O \end{pmatrix} \right]_m \left[ R_3 - C \begin{pmatrix} O \\ \| \\ O \end{pmatrix} \right]_n R_4 - C \begin{pmatrix} O \\ \| \\ OR_2 \end{pmatrix} \qquad \text{Formula VII}$$

wherein
m is an integer equal to or greater than 1;
n is an integer equal to or greater than 0;
$R_1$, independently for each occurrence, is an optionally substituted alkyl that is saturated or unsaturated, branched or unbranched;

$R_2$ is selected from hydrogen and optionally substituted alkyl that is saturated or unsaturated, and branched or unbranched; and $R_3$ and $R_4$, independently for each occurrence, are selected from optionally substituted alkyl that is saturated or unsaturated, and branched or unbranched, wherein at least one of $R_1$ is epoxidized or substituted with one or more of a hydroxy group or an alkoxy group.

DETAILED DESCRIPTION

The estolide compounds and compositions described herein may exhibit superior properties when compared to other lubricant compositions. Exemplary compositions include, but are not limited to, coolants, fire-resistant and/or non-flammable fluids, dielectric fluids such as transformer fluids, greases, drilling fluids, crankcase oils, hydraulic fluids, passenger car motor oils, 2- and 4-stroke lubricants, metalworking fluids, food-grade lubricants, refrigerating fluids, compressor fluids, and plasticized compositions.

The use of lubricants and lubricating fluid compositions may result in the dispersion of such fluids, compounds, and/or compositions in the environment. Petroleum base oils used in common lubricant compositions, as well as additives, are typically non-biodegradable and can be toxic. The present disclosure provides for the preparation and use of compositions comprising partially or fully bio-degradable base oils, including base oils comprising one or more estolides.

In certain embodiments, the lubricants and/or compositions comprising one or more estolides are partially or fully biodegradable and thereby pose diminished risk to the environment. In certain embodiments, the lubricants and/or compositions meet guidelines set for by the Organization for Economic Cooperation and Development (OECD) for degradation and accumulation testing. The OECD has indicated that several tests may be used to determine the "ready biodegradability" of organic chemicals. Aerobic ready biodegradability by OECD 301D measures the mineralization of the test sample to $CO_2$ in closed aerobic microcosms that simulate an aerobic aquatic environment, with microorganisms seeded from a waste-water treatment plant. OECD 301D is considered representative of most aerobic environments that are likely to receive waste materials. Aerobic "ultimate biodegradability" can be determined by OECD 302D. Under OECD 302D, microorganisms are pre-acclimated to biodegradation of the test material during a pre-incubation period, then incubated in sealed vessels with relatively high concentrations of microorganisms and enriched mineral salts medium. OECD 302D ultimately determines whether the test materials are completely biodegradable, albeit under less stringent conditions than "ready biodegradability" assays.

As used in the present specification, the following words, phrases and symbols are generally intended to have the meanings as set forth below, except to the extent that the context in which they are used indicates otherwise. The following abbreviations and terms have the indicated meanings throughout:

A dash ("-") that is not between two letters or symbols is used to indicate a point of attachment for a substituent. For example, —C(O)NH$_2$ is attached through the carbon atom.

"Alkoxy" by itself or as part of another substituent refers to a radical —OR$^{31}$ where R$^{31}$ is alkyl, cycloalkyl, cycloalkylalkyl, aryl, or arylalkyl, which can be substituted, as defined herein. In some embodiments, alkoxy groups have from 1 to 8 carbon atoms. In some embodiments, alkoxy groups have 1, 2, 3, 4, 5, 6, 7, or 8 carbon atoms. Examples of alkoxy groups include, but are not limited to, methoxy, ethoxy, propoxy, butoxy, cyclohexyloxy, and the like.

"Alkyl" by itself or as part of another substituent refers to a saturated or unsaturated, branched, or straight-chain monovalent hydrocarbon radical derived by the removal of one hydrogen atom from a single carbon atom of a parent alkane, alkene, or alkyne. Examples of alkyl groups include, but are not limited to, methyl; ethyls such as ethanyl, ethenyl, and ethynyl; propyls such as propan-1-yl, propan-2-yl, prop-1-en-1-yl, prop-1-en-2-yl, prop-2-en-1-yl (allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like.

Unless otherwise indicated, the term "alkyl" is specifically intended to include groups having any degree or level of saturation, i.e., groups having exclusively single carbon-carbon bonds, groups having one or more double carbon-carbon bonds, groups having one or more triple carbon-carbon bonds, and groups having mixtures of single, double, and triple carbon-carbon bonds. Where a specific level of saturation is intended, the terms "alkanyl," "alkenyl," and "alkynyl" are used. In certain embodiments, an alkyl group comprises from 1 to 40 carbon atoms, in certain embodiments, from 1 to 22 or 1 to 18 carbon atoms, in certain embodiments, from 1 to 16 or 1 to 8 carbon atoms, and in certain embodiments from 1 to 6 or 1 to 3 carbon atoms. In certain embodiments, an alkyl group comprises from 8 to 22 carbon atoms, in certain embodiments, from 8 to 18 or 8 to 16. In some embodiments, the alkyl group comprises from 3 to 20 or 7 to 17 carbons. In some embodiments, the alkyl group comprises 1, 2, 3, 4, 5, 6, 7, 8, 9, 10, 11, 12, 13, 14, 15, 16, 17, 18, 19, 20, 21, or 22 carbon atoms.

"Aryl" by itself or as part of another substituent refers to a monovalent aromatic hydrocarbon radical derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes 5- and 6-membered carbocyclic aromatic rings fused to a 5- to 7-membered non-aromatic heterocycloalkyl ring containing one or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Examples of aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, an aryl group can comprise from 5 to 20 carbon atoms, and in certain embodiments, from 5 to 12 carbon atoms. In certain embodiments, an aryl group can comprise 5, 6, 7, 8, 9, 10, 11, 12, 13, 14, 15, 16, 17, 18, 19, or 20 carbon atoms. Aryl, however, does not encompass or overlap in any way with heteroaryl, separately defined herein. Hence, a multiple ring system in which one or more carbocyclic aromatic rings is fused to a heterocycloalkyl aromatic ring, is heteroaryl, not aryl, as defined herein.

"Arylalkyl" by itself or as part of another substituent refers to an acyclic alkyl radical in which one of the hydrogen atoms bonded to a carbon atom, typically a terminal or sp$^3$ carbon atom, is replaced with an aryl group. Examples of arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl, and the like. Where specific alkyl moieties are intended, the nomenclature arylalkanyl, arylalkenyl, or arylalkynyl is used. In certain embodiments, an arylalkyl group is $C_{7-30}$ arylalkyl, e.g., the alkanyl, alkenyl, or alkynyl moiety of the arylalkyl group is $C_{1-10}$ and the aryl moiety is $C_{6-20}$, and in certain embodiments, an arylalkyl group is $C_{7-20}$ arylalkyl, e.g., the alkanyl, alkenyl, or alkynyl moiety of the arylalkyl group is $C_{1-8}$ and the aryl moiety is $C_{6-12}$.

Estolide "base oil" and "base stock", unless otherwise indicated, refer to any composition comprising one or more estolide compounds. It should be understood that an estolide "base oil" or "base stock" is not limited to compositions for a particular use, and may generally refer to compositions comprising one or more estolides, including mixtures of estolides. Estolide base oils and base stocks can also include compounds other than estolides.

"Compounds" refers to compounds encompassed by structural Formula I-VII herein and includes any specific compounds within the formula whose structure is disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore may exist as stereoisomers such as double-bond isomers (i.e., geometric isomers), enantiomers, or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to the skilled artisan.

For the purposes of the present disclosure, "chiral compounds" are compounds having at least one center of chirality (i.e. at least one asymmetric atom, in particular at least one asymmetric C atom), having an axis of chirality, a plane of chirality or a screw structure. "Achiral compounds" are compounds which are not chiral.

Compounds of Formula I-VII include, but are not limited to, optical isomers of compounds of Formula I-VII, racemates thereof, and other mixtures thereof. In such embodiments, the single enantiomers or diastereomers, i.e., optically active forms, can be obtained by asymmetric synthesis or by resolution of the racemates. Resolution of the racemates may be accomplished by, for example, chromatography, using, for example a chiral high-pressure liquid chromatography (HPLC) column. However, unless otherwise stated, it should be assumed that Formula I-VII cover all asymmetric variants of the compounds described herein, including isomers, racemates, enantiomers, diastereomers, and other mixtures thereof. In addition, compounds of Formula I-VII include Z- and E-forms (e.g., cis- and trans-forms) of compounds with double bonds. The compounds of Formula I-VII may also exist in several tautomeric forms including the enol form, the keto form, and mixtures thereof. Accordingly, the chemical structures depicted herein encompass all possible tautomeric forms of the illustrated compounds.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Examples of cycloalkyl groups include, but are not limited to, groups derived from cyclopropane, cyclobutane, cyclopentane, cyclohexane, and the like. In certain embodiments, a cycloalkyl group is $C_{3-15}$ cycloalkyl, and in certain embodiments, $C_{3-12}$ cycloalkyl or $C_{5-12}$ cycloalkyl. In certain embodiments, a cycloalkyl group is a $C_5$, $C_6$, $C_7$, $C_8$, $C_9$, $C_{10}$, $C_{11}$, $C_{12}$, $C_{13}$, $C_{14}$, or $C_{15}$ cycloalkyl.

"Cycloalkylalkyl" by itself or as part of another substituent refers to an acyclic alkyl radical in which one of the hydrogen atoms bonded to a carbon atom, typically a terminal or spa carbon atom, is replaced with a cycloalkyl group. Where specific alkyl moieties are intended, the nomenclature cycloalkylalkanyl, cycloalkylalkenyl, or cycloalkylalkynyl is used. In certain embodiments, a cycloalkylalkyl group is $C_{7-30}$ cycloalkylalkyl, e.g., the alkanyl, alkenyl, or alkynyl moiety of the cycloalkylalkyl group is $C_{1-10}$ and the cycloalkyl moiety is $C_{6-20}$, and in certain embodiments, a cycloalkylalkyl group is $C_{7-20}$ cycloalkylalkyl, e.g., the alkanyl, alkenyl, or alkynyl moiety of the cycloalkylalkyl group is $C_{1-8}$ and the cycloalkyl moiety is $C_{4-20}$ or $C_{6-12}$.

"Halogen" refers to a fluoro, chloro, bromo, or iodo group.

"Heteroaryl" by itself or as part of another substituent refers to a monovalent heteroaromatic radical derived by the removal of one hydrogen atom from a single atom of a parent heteroaromatic ring system. Heteroaryl encompasses multiple ring systems having at least one aromatic ring fused to at least one other ring, which can be aromatic or non-aromatic in which at least one ring atom is a heteroatom. Heteroaryl encompasses 5- to 12-membered aromatic, such as 5- to 7-membered, monocyclic rings containing one or more, for example, from 1 to 4, or in certain embodiments, from 1 to 3, heteroatoms chosen from N, O, and S, with the remaining ring atoms being carbon; and bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring. For example, heteroaryl includes a 5- to 7-membered heterocycloalkyl, aromatic ring fused to a 5- to 7-membered cycloalkyl ring. For such fused, bicyclic heteroaryl ring systems wherein only one of the rings contains one or more heteroatoms, the point of attachment may be at the heteroaromatic ring or the cycloalkyl ring. In certain embodiments, when the total number of N, S, and O atoms in the heteroaryl group exceeds one, the heteroatoms are not adjacent to one another. In certain embodiments, the total number of N, S, and O atoms in the heteroaryl group is not more than two. In certain embodiments, the total number of N, S, and O atoms in the aromatic heterocycle is not more than one. Heteroaryl does not encompass or overlap with aryl as defined herein.

Examples of heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, a heteroaryl group is from 5- to 20-membered heteroaryl, and in certain embodiments from 5- to 12-membered heteroaryl or from 5- to 10-membered heteroaryl. In certain embodiments, a heteroaryl group is a 5-, 6-, 7-, 8-, 9-, 10-, 11-, 12-, 13-, 14-, 15-, 16-, 17-, 18-, 19-, or 20-membered heteroaryl. In certain embodiments heteroaryl groups are those derived from thiophene, pyrrole, benzothiophene, benzofuran, indole, pyridine, quinoline, imidazole, oxazole, and pyrazine.

"Heteroarylalkyl" by itself or as part of another substituent refers to an acyclic alkyl radical in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl, or heteroarylalkynyl is used. In certain embodiments, a heteroarylalkyl group is a 6- to 30-membered heteroarylalkyl, e.g., the alkanyl, alkenyl, or alkynyl moiety of the heteroarylalkyl is 1- to 10-membered and the heteroaryl moiety is a 5- to 20-membered heteroaryl, and in certain embodiments, 6- to 20-membered heteroarylalkyl, e.g., the alkanyl, alkenyl, or alkynyl moiety of the heteroarylalkyl is 1- to 8-membered and the heteroaryl moiety is a 5- to 12-membered heteroaryl.

"Heterocycloalkyl" by itself or as part of another substituent refers to a partially saturated or unsaturated cyclic alkyl radical in which one or more carbon atoms (and any associated hydrogen atoms) are independently replaced with the same or different heteroatom. Examples of heteroatoms to replace the carbon atom(s) include, but are not limited to, N, P, O, S, Si, etc. Where a specific level of saturation is intended, the nomenclature "heterocycloalkanyl" or "heterocycloalkenyl" is used. Examples of heterocycloalkyl groups include, but are not limited to, groups derived from epoxides, azirines, thiiranes, imidazolidine, morpholine, piperazine, piperidine, pyrazolidine, pyrrolidine, quinuclidine, and the like.

"Heterocycloalkylalkyl" by itself or as part of another substituent refers to an acyclic alkyl radical in which one of the hydrogen atoms bonded to a carbon atom, typically a terminal or sp$^3$ carbon atom, is replaced with a heterocycloalkyl group. Where specific alkyl moieties are intended, the nomenclature heterocycloalkylalkanyl, heterocycloalkylalkenyl, or heterocycloalkylalkynyl is used. In certain embodiments, a heterocycloalkylalkyl group is a 6- to 30-membered heterocycloalkylalkyl, e.g., the alkanyl, alkenyl, or alkynyl moiety of the heterocycloalkylalkyl is 1- to 10-membered and the heterocycloalkyl moiety is a 5- to 20-membered heterocycloalkyl, and in certain embodiments, 6- to 20-membered heterocycloalkylalkyl, e.g., the alkanyl, alkenyl, or alkynyl moiety of the heterocycloalkylalkyl is 1- to 8-membered and the heterocycloalkyl moiety is a 5- to 12-membered heterocycloalkyl.

"Mixture" refers to a collection of molecules or chemical substances. Each component in a mixture can be independently varied. A mixture may contain, or consist essentially of, two or more substances intermingled with or without a constant percentage composition, wherein each component may or may not retain its essential original properties, and where molecular phase mixing may or may not occur. In mixtures, the components making up the mixture may or may not remain distinguishable from each other by virtue of their chemical structure.

"Parent aromatic ring system" refers to an unsaturated cyclic or polycyclic ring system having a conjugated π (pi) electron system. Included within the definition of "parent aromatic ring system" are fused ring systems in which one or more of the rings are aromatic and one or more of the rings are saturated or unsaturated, such as, for example, fluorene, indane, indene, phenalene, etc. Examples of parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Parent heteroaromatic ring system" refers to a parent aromatic ring system in which one or more carbon atoms (and any associated hydrogen atoms) are independently replaced with the same or different heteroatom. Examples of heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Examples of parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Substituted" refers to a group in which one or more hydrogen atoms are independently replaced with the same or different substituent(s). Examples of substituents include, but are not limited to, —R$^{64}$, —R$^{60}$, —O$^-$, —OH, =O, —OR$^{60}$, —SR$^{60}$, —S$^-$, =S, —NR$^{60}$R$^{61}$, =NR$^{60}$, —CN, —CF$_3$, —OCN, —SCN, —NO, —NO$_2$, =N$_2$, —N$_3$, —S(O)$_2$O$^-$, —S(O)$_2$OH, —S(O)$_2$R$^{60}$, —OS(O$_2$)O$^-$, -OS(O)$_2$R$^{60}$, —P(O)(O$^-$)$_2$, —P(O)(OR$^{60}$)(O$^-$), —OP(O)(OR$^{60}$)(OR$^{61}$), —C(O)R$^{60}$, —C(S)R$^{60}$, —C(O)OR$^{60}$, —C(O)NR$^{60}$R$^{61}$, —C(O)O$^-$, —C(S)OR$^{60}$, —NR$^{62}$C(O)NR$^{60}$R$^{61}$, —NR$^{62}$C(S)NR$^{60}$R$^{61}$, —NR$^{62}$C(NR$^{63}$)NR$^{60}$R$^{61}$, —C(NR$^{62}$)NR$^{60}$R$^{61}$, —S(O)$_2$, NR$^{60}$R$^{61}$, —NR$^{63}$S(O)$_2$R$^{60}$, —NR$^{63}$C(O)R$^{60}$, and —S(O)R$^{60}$;

wherein each —R$^{64}$ is independently a halogen; each R$^{60}$ and R$^{61}$ are independently alkyl, substituted alkyl, alkoxy, substituted alkoxy, cycloalkyl, substituted cycloalkyl, heterocycloalkyl, substituted heterocycloalkyl, aryl, substituted aryl, heteroaryl, substituted heteroaryl, arylalkyl, substituted arylalkyl, heteroarylalkyl, or substituted heteroarylalkyl, or R$^{60}$ and R$^{61}$ together with the nitrogen atom to which they are bonded form a heterocycloalkyl, substituted heterocycloalkyl, heteroaryl, or substituted heteroaryl ring, and R$^{62}$ and R$^{63}$ are independently alkyl, substituted alkyl, aryl, substituted aryl, arylalkyl, substituted arylalkyl, cycloalkyl, substituted cycloalkyl, heterocycloalkyl, substituted heterocycloalkyl, heteroaryl, substituted heteroaryl, heteroarylalkyl, or substituted heteroarylalkyl, or R$^{62}$ and R$^{63}$ together with the atom to which they are bonded form one or more heterocycloalkyl, substituted heterocycloalkyl, heteroaryl, or substituted heteroaryl rings;

wherein the "substituted" substituents, as defined above for R$^{60}$R$^{61}$, R$^{62}$, and R$^{63}$, are substituted with one or more, such as one, two, or three, groups independently selected from alkyl, -alkyl-OH, —O-haloalkyl, -alkyl-$NH_2$, alkoxy, cycloalkyl, cycloalkylalkyl, heterocycloalkyl, heterocycloalkylalkyl, aryl, heteroaryl, arylalkyl, heteroarylalkyl, —$O^-$, —OH, =O, —O-alkyl, —O-aryl, —O-heteroarylalkyl, —O-cycloalkyl, —O-heterocycloalkyl, —SH, —$S^-$, =S, —S-alkyl, —S-aryl, —S-heteroarylalkyl, —S-cycloalkyl, —S-heterocycloalkyl, —$NH_2$, =NH, —CN, —$CF_3$, —OCN, —SCN, —NO, —$NO_2$, =$N_2$, —$N_3$, —$S(O)_2O^-$, —$S(O)_2$, —$S(O)_2OH$, —$OS(O_2)O^-$, —$SO_2$(alkyl), —$SO_2$(phenyl), —$SO_2$(haloalkyl), —$SO_2NH_2$, —$SO_2NH$(alkyl), —$SO_2NH$(phenyl), —$P(O)(O^-)_2$, —$P(O)(O$-alkyl$)(O^-)$, —OP(O)(O-alkyl)(O-alkyl), —$CO_2H$, —C(O)O(alkyl), —CON(alkyl)(alkyl), —CONH(alkyl), —$CONH_2$, —C(O)(alkyl), —C(O)(phenyl), —C(O)(haloalkyl), —OC(O)(alkyl), —N(alkyl)(alkyl), —NH(alkyl), —N(alkyl)(alkylphenyl), —NH(alkylphenyl), —NHC(O)(alkyl), —NHC(O)(phenyl), —N(alkyl)C(O)(alkyl), and —N(alkyl)C(O)(phenyl).

As used in this specification and the appended claims, the articles "a," "an," and "the" include plural referents unless expressly and unequivocally limited to one referent.

The term "fatty acid" refers to any natural or synthetic carboxylic acid comprising an alkyl chain that may be saturated, monounsaturated, or polyunsaturated, and may have straight or branched chains. The fatty acid may also be substituted. "Fatty acid," as used herein, includes short chain alkyl carboxylic acid including, for example, acetic acid, propionic acid, etc.

All numerical ranges herein include all numerical values and ranges of all numerical values within the recited range of numerical values.

The present disclosure relates to estolide compounds, compositions, and methods of making the same. In certain embodiments, the present disclosure relates to biosynthetic estolides having one or more desirable physical properties, such as improved viscometrics, pour point, oxidative stability, hydrolytic stability, and/or viscosity index. In certain embodiments, the present disclosure relates to new methods of preparing estolide compounds exhibiting such properties. In certain embodiments, the compounds and compositions comprise poly-capped estolides.

In certain embodiments, the estolides comprise at least one compound selected from Formula I:

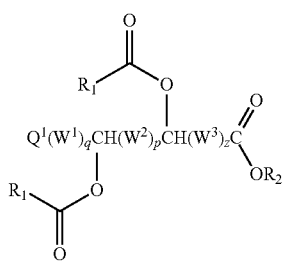

Formula I wherein
z is an integer selected from 0, 1, 2, 3, 4, 5, 6, 7, 8, 9, 10, 11, 12, 13, 14 and 15;
p is an integer selected from 0, 1, 2, 3, 4, 5, 6, 7, 8, 9, 10, 11, 12, 13, 14 and 15;
q is an integer selected from 0, 1, 2, 3, 4, 5, 6, 7, 8, 9, 10, 11, 12, 13, 14 and 15;

$R_1$, independently for each occurrence, is an optionally substituted alkyl that is saturated or unsaturated, and branched or unbranched; and $R_2$ is selected from hydrogen, optionally substituted alkyl that is saturated or unsaturated, and branched or unbranched, and a substituent represented by Formula II:

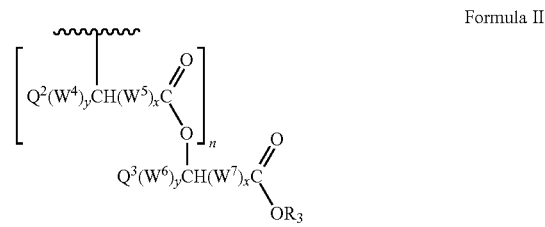

Formula II wherein
x is, independently for each occurrence, an integer selected from 0, 1, 2, 3, 4, 5, 6, 7, 8, 9, 10, 11, 12, 13, 14, 15, 16, 17, 18, 19, and 20;
y is, independently for each occurrence, an integer selected from 0, 1, 2, 3, 4, 5, 6, 7, 8, 9, 10, 11, 12, 13, 14, 15, 16, 17, 18, 19, and 20;
n is 0 or greater than 0;
$R_3$ is selected from hydrogen and optionally substituted alkyl that is saturated or unsaturated, and branched or unbranched;
$W^1$, $W^2$, $W^3$, $W^4$, $W^5$, $W^6$, and $W^7$, independently for each occurrence, are selected from —$CH_2$— and —CH=CH—; and
$Q^1$, $Q^2$, and $Q^3$, independently for each occurrence, are selected from hydrogen and —$CH_3$,
wherein each fatty acid chain residue of said at least one compound is independently optionally substituted.

In certain embodiments, the at least one compound of Formula I is selected from compounds of Formula III:

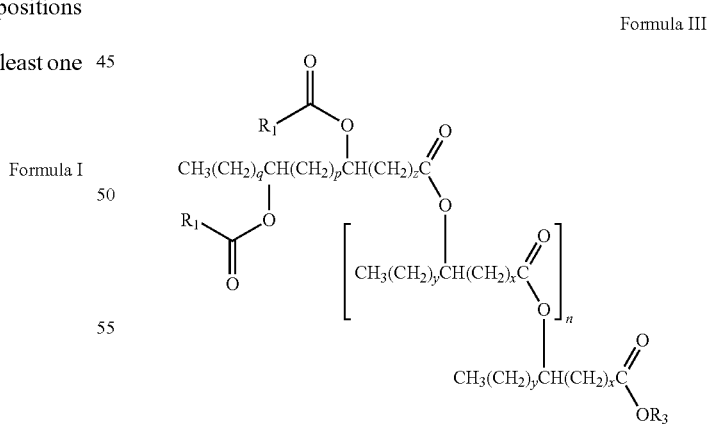

Formula III wherein
x is, independently for each occurrence, an integer selected from 1, 2, 3, 4, 5, 6, 7, 8, 9 and 10;
y is, independently for each occurrence, an integer selected from 1, 2, 3, 4, 5, 6, 7, 8, 9 and 10; and
n is an integer selected from 0, 1, 2, 3, 4, 5, 6, 7 and 8.

In certain embodiments, the estolides comprise at least one compound selected from Formula IV:

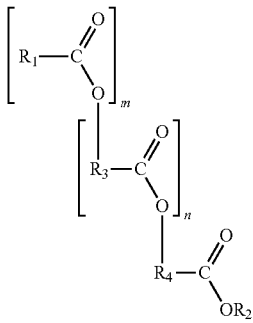

Formula IV wherein
n is equal to or greater than 0;
m is equal to or greater than 2;
$R_2$ is selected from hydrogen and optionally substituted alkyl that is saturated or unsaturated, and branched or unbranched; and
$R_1$, $R_3$ and $R_4$, independently for each occurrence, are selected from optionally substituted alkyl that is saturated or unsaturated, and branched or unbranched.

In certain embodiments, the estolides comprise at least one compound selected from Formula V:

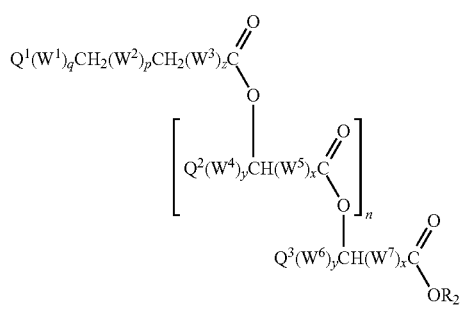

Formula V wherein
$W^1$, $W^2$, $W^3$, $W^4$, $W^5$, $W^6$, and $W^7$, independently for each occurrence, are selected from —CH$_2$—, —CH=CH—, and

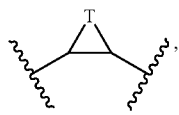

provided that at least one of $W^1$, $W^2$, $W^3$, $W^4$, $W^5$, $W^6$, or $W^7$ is

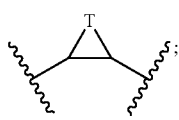

T is O;
$Q^1$, $Q^2$, and $Q^3$, independently for each occurrence, are selected from hydrogen and —CH$_3$;

z is an integer selected from 0 to 15;
p is an integer selected from 0 to 15;
q is an integer selected from 0 to 15;
x is, independently for each occurrence, an integer selected from 0 to 20;
y is, independently for each occurrence, an integer selected from 0 to 20;
n is equal to or greater than 0; and
$R_2$ is selected from hydrogen and optionally substituted alkyl that is saturated or unsaturated, and branched or unbranched,
wherein each fatty acid chain residue of said at least one compound is independently optionally substituted.

In certain embodiments, the estolides comprise at least one compound selected from Formula VI:

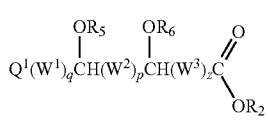

Formula VI wherein
z is an integer selected from 0, 1, 2, 3, 4, 5, 6, 7, 8, 9, 10, 11, 12, 13, 14 and 15;
p is an integer selected from 0, 1, 2, 3, 4, 5, 6, 7, 8, 9, 10, 11, 12, 13, 14 and 15;
q is an integer selected from 0, 1, 2, 3, 4, 5, 6, 7, 8, 9, 10, 11, 12, 13, 14 and 15;
$R_5$ and $R_6$ are independently selected from hydrogen, —C(O)$R_1$, and an optionally substituted alkyl that is saturated or unsaturated, and branched or unbranched;
$R_1$ is and optionally substituted alkyl that is saturated or unsaturated, and branched or unbranched; and
$R_2$ is selected from hydrogen, optionally substituted alkyl that is saturated or unsaturated, and branched or unbranched, and a substituent represented by graphic Formula II:

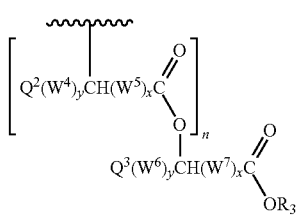

Formula II wherein
x is, independently for each occurrence, an integer selected from 0, 1, 2, 3, 4, 5, 6, 7, 8, 9, 10, 11, 12, 13, 14, 15, 16, 17, 18, 19, and 20;
y is, independently for each occurrence, an integer selected from 0, 1, 2, 3, 4, 5, 6, 7, 8, 9, 10, 11, 12, 13, 14, 15, 16, 17, 18, 19, and 20;
n is 0 or greater than 0;
$R_3$ is selected from hydrogen and optionally substituted alkyl that is saturated or unsaturated, and branched or unbranched;
$W^1$, $W^2$, $W^3$, $W^4$, $W^5$, $W^6$, and $W^7$, independently for each occurrence, are selected from —CH$_2$— and —CH=CH—; and
$Q^1$, $Q^2$, and $Q^3$, independently for each occurrence, are selected from hydrogen and —CH$_3$, wherein each fatty acid chain residue of said at least one compound is independently optionally substituted.

In certain embodiments, the estolides comprise at least one compound selected from Formula VII:

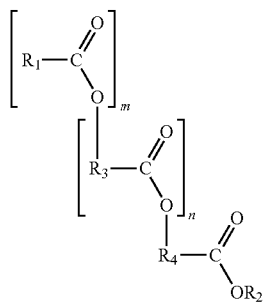

Formula VII wherein m is an integer equal to or greater than 1;

n is an integer equal to or greater than 0;

$R_1$, independently for each occurrence, is an optionally substituted alkyl that is saturated or unsaturated, branched or unbranched;

$R_2$ is selected from hydrogen and optionally substituted alkyl that is saturated or unsaturated, and branched or unbranched; and $R_3$ and $R_4$, independently for each occurrence, are selected from optionally substituted alkyl that is saturated or unsaturated, and branched or unbranched, wherein at least one of $R_1$ is epoxidized or substituted with one or more of a hydroxy group or an alkoxy group.

In certain embodiments, the composition comprises at least one estolide of Formula I, III, IV, V, or VII, where $R_1$ is hydrogen.

The terms "chain" or "fatty acid chain" or "fatty acid chain residue," as used with respect to the estolide compounds of Formulas I-VII, refer to one or more of the fatty acid residues incorporated in estolide compounds, e.g., $R_3$ or $R_4$ of Formulas IV and VII, the structures represented by $CH_3(CH_2)_y CH(CH_2)_x C(O)O-$ and $CH_3(CH_2)_q CH(CH_2)_p CH(CH_2)_z C(O)O$ in Formula III, the structures represented by $Q^1(W^1)_q CH(W^2)_p CH(W^3)_z C(O)O-$, $Q^2(W^4)_y CH(W^5)_x C(O)O-$, and $Q^3(W^6)_y CH(W^7)_x C(O)O-$ in Formulas I and II, the structures represented by $Q^1(W^1)_q CH_2(W^2)_p CH_2(W^3)_z C(O)O-$, $Q^2(W^4)_y CH(W^5)_x C(O)O-$, and $Q^3(W^6)_y CH(W^7)_x C(O)O-$ in Formula V, and the structure represented by $Q^1(W^1)_q CH(OR_5)(W^2)_p CH(OR_6)(W^3)_z C(O)O-$ in Formula VI.

The residues $R_1 C(O)O-$ in Formulas I, III, IV, and VII (and optionally Formula VI) at the top of each Formula shown is an example of what may be referred to as "caps" or "capping materials," as it "caps" the top of the estolide. In certain embodiments, the "caps" or "capping groups" are fatty acids. In certain embodiments, the capping group may be an organic acid residue of general formula $Q^1(W^1)_q CH_2(W^2)_p CH_2(W^3)_z-C(O)-O-$, e.g., as reflected in Formula V. Similarly, the capping group may be an organic acid residue of general formula $-OC(O)$-alkyl, i.e., a carboxylic acid with an substituted or unsubstituted, saturated or unsaturated, and/or branched or unbranched alkyl as defined herein. In certain embodiments, the capping groups, regardless of size, are substituted or unsubstituted, saturated or unsaturated, and/or branched or unbranched. The caps or capping materials may also be referred to as the primary or alpha (α) chains. In certain embodiments the estolides are described as "poly-capped," wherein the compounds comprise two or more primary chains. With respect to Formula IV, an exemplary "poly-capped" estolide would include embodiments wherein m=2 and two $R_1 C(O)O-$ residues are linked to $R_3$.

Depending on the manner in which the estolide is synthesized, the caps may be the only residues in the resulting estolide that are unsaturated. In certain embodiments, it may be desirable to use saturated organic or fatty-acid caps to increase the overall saturation of the estolide and/or to increase the resulting estolide's stability. For example, in certain embodiments, it may be desirable to provide a saturated capped estolide by epoxidizing, sulfurizing, and/or hydrogenating an unsaturated cap using any suitable methods available to those of ordinary skill in the art. Epoxidizing, sulfurizing, and/or hydrogenating may be used with various sources of the fatty-acid feedstock, which may include mono- and/or polyunsaturated fatty acids.

In certain embodiments, epoxidized estolides can be prepared by epoxidizing one or more estolide compounds having at least one site of unsaturation. In certain embodiments, the epoxidizing may be accomplished using any of the methods generally known to those of ordinary skill in the art, such as using hydrogen peroxide and/or formic acid, or those methods involving one or more percarboxylic acids such as m-chloroperbenzoic acid, peracetic acid, or performic acid. Exemplary epoxidation methods also include those set forth in D. Swern, *Organic Peroxides*, Volume 2, 355-533, Interscience Publishers, 1971, which is incorporated by reference in its entirety for all purposes.

Without being bound to any particular theory, in certain embodiments, epoxidizing the estolide may help to improve the solubility and/or miscibility of the compound in certain compositions, such as those containing polymeric materials. Alternatively, in certain embodiments, epoxidizing an estolide may provide for an intermediate compound, wherein the epoxide residue may be opened by reacting it with one or more compounds or compositions. For example, in certain embodiments, the epoxide residue of an epoxy estolide is opened to provide a mono-hydroxy estolide or a dihydroxy estolide. In certain embodiments, exposing an epoxy estolide to aqueous acid conditions will provide a dihydroxy estolide. In certain embodiments, reacting an epoxy estolide with an alcohol (e.g., fatty alcohol) under acidic conditions will provide a mono-hydroxy estolide substituted with an alkoxy group. In certain embodiments, the epoxide residue may be opened by reacting the epoxy estolide with a carboxylic acid (e.g., fatty acid) to provide the mono-hydroxy estolide. In certain embodiments, estolides having free hydroxy groups may be acylated to provide poly-capped estolides.

In certain embodiments, it may be desirable to provide a method of preparing a saturated capped estolide by hydrogenating one or more of the unsaturated caps using any suitable methods available to those of ordinary skill in the art. Hydrogenation may be used with various sources of the fatty-acid feedstock, which may include mono- and/or polyunsaturated fatty acids. Without being bound to any particular theory, in certain embodiments, hydrogenating the estolide may help to improve the overall stability of the molecule. However, a fully-hydrogenated estolide, such as an estolide with a larger fatty acid cap, may exhibit increased pour point temperatures. In certain embodiments, it may be desirable to offset any loss in desirable pour-point characteristics by using shorter, saturated capping materials.

The structure $R_4 C(O)O-$ of Formulas IV and VII, structure $CH_3(CH_2)_y CH(CH_2)_x C(O)O-$ of Formula III, structure $Q^1(W^1)_q CH(W^2)_p CH(W^3)_z C(O)O-$ of Formula I and VI (when $R_2$ is not the structure of Formula II), and structure $Q^3(W^6)_y CH(W^7)_x C(O)O$— of Formulas II and V serve as the "base" or "base chain residue" of the estolide. Depending on the manner in which the estolide is synthesized, the base organic acid or fatty acid residue may be the only residue that remains in its free-acid form after the initial synthesis of the estolide. However, in certain embodiments, in an effort to alter or improve the properties of the estolide, the free acid may be reacted with any number of substituents. For example, it may be desirable to react the free acid estolide with alcohols, glycols, amines, or other suitable reactants to provide the corresponding ester, amide, or other reaction products. The base or base chain residue may also be referred to as tertiary or gamma ($\gamma$) chains.

The structure $R_3C(O)O$— of Formulas IV and VII, and the structure $Q^2(W^4)_y CH(W^5)_x C(O)O$— of Formulas II and V are linking residues that link the capping material and the base fatty-acid residue. Depending on the manner in which the estolide is prepared, a linking residue may be a fatty acid and may initially be in an unsaturated form during synthesis. In some embodiments, the estolide will be formed when a catalyst is used to produce a carbocation at the fatty acid's site of unsaturation, which is followed by nucleophilic attack on the carbocation by the carboxylic acid group of another fatty acid. In certain embodiments, the formation of the carbocation will result in a mixture of estolide isomers, wherein the bond between two fatty acid residues takes place at one of two available carbon linking sites (e.g., estolide linkage at primarily the (18:1 n−9) and (18:1 n−10) positions of oleic acid residues). In certain embodiments, polyunsaturated fatty acids may provide multiple carbocations for the addition of two or more fatty acids to the polyunsaturated residue to provide, for example, poly-capped estolides. In some embodiments, it may be desirable to have a linking fatty acid that is monounsaturated so that when the fatty acids link together, all of the sites of unsaturation are eliminated. The linking residue(s) may also be referred to as secondary or beta ($\beta$) chains.

In certain embodiments, the caps comprise two or more acetyl caps, the linking residue(s) is one or more fatty acid residues, and the base chain residue is a fatty acid residue. In certain embodiments, the linking residues present in an estolide differ from one another. In certain embodiments, one or more of the linking residues differs from the base chain residue. In certain embodiments, the estolide does not comprise a linking residue and is in its dimer form, wherein the compound comprises two or more organic (e.g., acetyl) or fatty-acid caps linked directly to a base residue.

As noted above, in certain embodiments, suitable unsaturated fatty acids for preparing the estolides may include any mono- or polyunsaturated fatty acid. For example, monounsaturated fatty acids, along with a suitable catalyst, will form a single carbocation of the addition of a second fatty acid, whereby a single link between two fatty acids (e.g., between $\beta$-chain and $\gamma$-chain, and $\beta$-chain and $\alpha$-chain) is formed. Suitable monounsaturated fatty acids may include, but are not limited to, palmitoleic (16:1), vaccenic (18:1), oleic acid (18: 1), eicosenoic acid (20:1), erucic acid (22:1), and nervonic acid (24:1). In addition, in certain embodiments, polyunsaturated fatty acids may be used to create estolides. Suitable polyunsaturated fatty acids may include, but are not limited to, hexadecatrienoic acid (16:3), alpha-linolenic acid (18:3), stearidonic acid (18:4), eicosatrienoic acid (20:3), eicosatetraenoic acid (20:4), eicosapentaenoic acid (20:5), heneicosapentaenoic acid (21:5), docosapentaenoic acid (22:5), docosahexaenoic acid (22:6), tetracosapentaenoic acid (24: 5), tetracosahexaenoic acid (24:6), linoleic acid (18:2), gamma-linoleic acid (18:3), eicosadienoic acid (20:2), dihomo-gamma-linolenic acid (20:3), arachidonic acid (20: 4), docosadienoic acid (20:2), adrenic acid (22:4), docosapentaenoic acid (22:5), tetracosatetraenoic acid (22:4), tetracosapentaenoic acid (24:5), pinolenic acid (18:3), podocarpic acid (20:3), rumenic acid (18:2), alpha-calendic acid (18:3), beta-calendic acid (18:3), jacaric acid (18:3), alpha-eleostearic acid (18:3), beta-eleostearic acid (18:3), catalpic acid (18: 3), punicic acid (18:3), rumelenic acid (18:3), alpha-parinaric acid (18:4), beta-parinaric acid (18:4), and bosseopentaenoic acid (20:5). In certain embodiments, hydroxy fatty acids may be polymerized or homopolymerized by reacting the carboxylic acid functionality of one fatty acid with the hydroxy functionality of a second fatty acid. Exemplary hydroxyl fatty acids include, but are not limited to, ricinoleic acid, 6-hydroxystearic acid, 9,10-dihydroxystearic acid, 12-hydroxystearic acid, and 14-hydroxystearic acid.

Because polyunsaturated fatty acids have more than one site of unsaturation, the resulting estolide may comprise unsaturated chains and/or chains substituted with two or more fatty acids. For example, preparing an estolide from linoleic and/or linolenic acid can result in estolides having two or more caps. In certain embodiments, linoleic and/or linolenic acid is reacted with an organic and/or fatty acid to provide an estolide having two or more caps. In some embodiments, the organic and/or fatty acid cap comprises a $C_1$-$C_{40}$ alkyl residue. In some embodiments, the organic acid cap is acetic acid. In some embodiment, the fatty acid cap comprises a $C_7$-$C_{17}$ alkyl residue.

The process for preparing the estolide compounds described herein may include the use of any natural or synthetic fatty acid source. However, it may be desirable to source the fatty acids from a renewable biological feedstock. Suitable starting materials of biological origin may include plant fats, plant oils, plant waxes, animal fats, animal oils, animal waxes, fish fats, fish oils, fish waxes, algal oils and mixtures thereof. Other potential fatty acid sources may include waste and recycled food-grade fats and oils, fats, oils, and waxes obtained by genetic engineering, fossil fuel based materials and other sources of the materials desired.

In certain embodiments, the estolide compounds described herein may be prepared from non-naturally occurring fatty acids derived from naturally occurring feedstocks. In certain embodiments, the estolides are prepared from synthetic fatty acid reactants derived from naturally occurring feedstocks such as vegetable oils. For example, the synthetic fatty acid reactants may be prepared by cleaving fragments from larger fatty acid residues occurring in natural oils such as triglycerides using, for example, a cross-metathesis catalyst and alpha-olefin(s). The resulting truncated fatty acid residue(s) may be liberated from the glycerine backbone using any suitable hydrolytic and/or transesterification processes known to those of skill in the art. An exemplary fatty acid reactant includes 9-dodecenoic acid, which may be prepared via the cross metathesis of an oleic acid residue with 1-butene. In certain embodiments, the estolide may be prepared from fatty acids having a terminal site of unsaturation (e.g., 9-decenoic acid), which may be prepared via the cross metathesis of an oleic acid residue with ethene.

In some embodiments, the estolide comprises fatty-acid chains of varying lengths. In some embodiments, z, p, and q are independently an integer selected from 0 to 15, 0 to 12, 0 to 8, 0 to 6, 0 to 4, and 0 to 2. For example, in some embodiments, z is an integer selected from 0 to 15, 0 to 12, and 0 to 8. In some embodiments, z is an integer selected from 7 and 8. In some embodiments, p is an integer selected from 0 to 15, 0 to 6, and 0 to 3. In some embodiments, p is an integer selected from 1, 2, and 3, or 4, 5, and 6. In some embodiments, q is an integer selected from 0 to 15, 0 to 6, and 0 to 3. In some embodiments, q is an integer selected from 2 and 3, or 5 and 6. In some embodiments, z, p and q, independently for each occurrence, are selected from 0, 1, 2, 3, 4, 5, 6, 6, 8, 9, 10, 11, 12, 13, 14 and 15. In some embodiments, z+p+q is an integer selected from 12 to 20. In some embodiments, z+p+q is 14. In certain embodiments, z+p+q is an integer selected from 7 and 8. In certain embodiments, z+p+q is an integer selected from 3 to 15, such as 5, 7, 14 or 15.

In some embodiments, x is, independently for each occurrence, an integer selected from 0 to 20, 0 to 18, 0 to 16, 0 to 14, 1 to 12, 1 to 10, 2 to 8, 6 to 8, or 4 to 6. In some embodiments, x is, independently for each occurrence, an integer selected from 7 and 8. In some embodiments, x is, independently for each occurrence, an integer selected from 0, 1, 2, 3, 4, 5, 6, 7, 8, 9, 10, 11, 12, 13, 14, 15, 16, 17, 18, 19, and 20.

In some embodiments, y is, independently for each occurrence, an integer selected from 0 to 20, 0 to 18, 0 to 16, 0 to 14, 1 to 12, 1 to 10, 2 to 8, 6 to 8, or 4 to 6. In some embodiments, y is, independently for each occurrence, an integer selected from 7 and 8. In some embodiments, x is, independently for each occurrence, an integer selected from 0, 1, 2, 3, 4, 5, 6, 7, 8, 9, 10, 11, 12, 13, 14, 15, 16, 17, 18, 19, and 20.

In some embodiments, x+y is, independently for each chain, an integer selected from 0 to 40, 0 to 20, 10 to 20, or 12 to 18. In some embodiments, x+y is, independently for each chain, an integer selected from 13 to 15. In some embodiments, x+y, for one or more of the fatty acid chain residues, is 15. In some embodiments, x+y is, independently for each chain, an integer selected from 6, 7, 8, 9, 10, 11, 12, 13, 14, 15, 16, 17, 18, 19, 20, 21, 22, 23, and 24.

In some embodiments, $W^1$, $W^2$, $W^3$, $W^4$, $W^5$, $W^6$, and $W^7$, independently for each occurrence, are selected from —$CH_2$— and —CH=CH—. In some embodiments, $W^3$, $W^5$, and $W^7$ for each occurrence are —$CH_2$—. In some embodiments, $W^4$ and $W^6$ for each occurrence are —$CH_2$—. In some embodiments, $W^1$ for each occurrence is —$CH_2$—. In some embodiments, $W^2$ for each occurrence is —$CH_2$—.

In some embodiments, the estolide compound may comprise any number of fatty acid residues to form an "n-mer" estolide. For example, the estolide compound of Formula IV may be in its dimer (n=0), trimer (n=1), tetramer (n=2), pentamer (n=3), hexamer (n=4), heptamer (n=5), octamer (n=6), nonamer (n=7), or decamer (n=8) form. In some embodiments, n is an integer selected from 0 to 20, 0 to 18, 0 to 16, 0 to 14, 0 to 12, 0 to 10, 0 to 8, or 0 to 6. In some embodiments, n is an integer selected from 0 to 4. In some embodiments, n is an integer that is equal to or greater than 1, wherein said at least one compound of Formula IV comprises the trimer. In some embodiments, n is an integer selected from 1 to 12, 1 to 8, or 1 to 4. In some embodiments, n is an integer selected from 0, 1, 2, 3, 4, 5, 6, 7, 8, 9, 10, 11, and 12.

In certain embodiments, the compounds of Formulas I/II and III represent subgenera of Formula IV. Thus, in some embodiments, reference to a compound of Formulas I/II and III in its "n-mer" form may be better understood when discussed in reference to Formula IV. By way of example, a compound of Formula I, when $R_2$ is selected from hydrogen and an alkyl group, may be described as being in its "dimer" form. That same compound can be described with reference to Formula IV, wherein m=2, n=0, and $R_4$ represents the group $Q^1(W^1)_q CH(W^2)_p CH(W^3)_z$—.

In certain embodiments, $Q^1$, $Q^2$, and $Q^3$, independently for each occurrence, are selected from hydrogen and —$CH_3$. For example, in certain embodiments, estolides of Formulas I/II are prepared from terminally-unsaturated fatty acids such as 9-decenoic acid. In certain embodiments, oligomerizing terminally-unsaturated fatty acids such as 9-decenoic acid will provide estolide intermediates having a fatty acid cap with a terminal site of unsaturation, which may be used to provide, e.g., a dihydroxy estolide variant that can be acylated to provide poly-capped estolides. Thus, in certain embodiments, $Q^1$ is hydrogen, and $Q^2$ and $Q^3$ are independently selected from hydrogen and —$CH_3$. In certain embodiments, q is 0 and $Q^1$ is hydrogen. In certain embodiments, $Q^1$, $Q^2$, and $Q^3$ are —$CH_3$.

In certain embodiments, $R_5$ and $R_6$, independently for each occurrence, are selected from hydrogen, —C(O)$R_1$, and an optionally substituted alkyl that is saturated or unsaturated, and branched or unbranched. In certain embodiments, $R_5$ and $R_6$ are hydrogen. In certain embodiments, $R_5$ and $R_6$ are independently selected from optionally substituted alkyl that is saturated or unsaturated, and branched or unbranched. In certain embodiments, $R_5$ and $R_6$ are independently selected from hydrogen and —C(O)$R_1$. In certain embodiments, $R_5$ and $R_6$ are independently selected from hydrogen and optionally substituted alkyl that is saturated or unsaturated, and branched or unbranched. In certain embodiments, $R_5$ and $R_6$ are independently selected from hydrogen and $C_1$-$C_{10}$ alkyl.

In some embodiments, $R_1$, independently for each occurrence, is an optionally substituted alkyl that is saturated or unsaturated, and branched or unbranched. In some embodiments, the alkyl group is a $C_1$ to $C_{40}$ alkyl, $C_1$ to $C_{22}$ alkyl or $C_1$ to $C_{17}$ alkyl. In some embodiments, the alkyl group is selected from $C_7$ to $C_{17}$ alkyl, $C_3$ to $C_{13}$ alkyl, or $C_5$ to $C_{11}$ alkyl. In some embodiments, each $R_1$ is independently selected from $C_1$ alkyl, $C_2$ alkyl, $C_3$ alkyl, $C_4$ alkyl, $C_5$ alkyl, $C_6$ alkyl, $C_7$ alkyl, $C_8$ alkyl, $C_9$ alkyl, $C_{10}$ alkyl, $C_{11}$ alkyl, $C_{12}$ alkyl, $C_{13}$ alkyl, $C_{14}$ alkyl, $C_{15}$ alkyl, $C_{16}$ alkyl, $C_{17}$ alkyl, $C_{18}$ alkyl, $C_{19}$ alkyl, $C_{20}$ alkyl, $C_{21}$ alkyl, $C_{22}$ alkyl, $C_{23}$ alkyl, and $C_{24}$ alkyl. In some embodiments, each $R_1$ is methyl. In some embodiments, $R_1$ is independently selected from $C_{13}$ to $C_{17}$ alkyl, such as from $C_{13}$ alkyl, $C_{15}$ alkyl, and $C_{17}$ alkyl.

It may be possible to manipulate one or more of the estolides' properties by altering the length of $R_1$ and/or its degree of saturation. However, the level of substitution on $R_1$ may also be altered to change or even improve the estolides' properties. Without being bound to any particular theory, it is believed that the presence of polar substituents on $R_1$, such as one or more hydroxy groups, may increase the viscosity of the estolide, while adversely increasing pour point. Accordingly, in some embodiments, $R_1$ will be unsubstituted or optionally substituted with a group that is not hydroxyl.

In some embodiments, the estolides of Formulas I/II, III, IV, V, and VI/II may be in their free-acid form, wherein $R_2$ and $R_3$ are hydrogen. With respect to Formula I, if $R_2$ is the substituent represented by Formula II described above, the resulting estolide will be in its free acid form when $R_3$ is hydrogen. However, in some embodiments, $R_2$ and $R_3$ are independently selected from optionally substituted alkyl that is saturated or unsaturated, and branched or unbranched. In some embodiments, the alkyl group is selected from $C_1$ to $C_{40}$, $C_1$ to $C_{22}$, $C_3$ to $C_{20}$, $C_1$ to $C_{18}$, or $C_6$ to $C_{12}$ alkyl. In some embodiments, $R_2$ and $R_3$ may be independently selected from $C_3$ alkyl, $C_4$ alkyl, $C_8$ alkyl, $C_{12}$ alkyl, $C_{16}$ alkyl, $C_{18}$ alkyl, and $C_{20}$ alkyl. For example, $R_2$ and $R_3$ may be branched, such as isopropyl, isobutyl, or 2-ethylhexyl. In some embodiments, $R_2$ and $R_3$ may be a larger alkyl group, branched or unbranched, comprising $C_{12}$ alkyl, $C_{16}$ alkyl, $C_{18}$ alkyl, or $C_{20}$ alkyl. Such groups at the $R_2$ or $R_3$ position may be derived from esterification of the free-acid estolide using the Jarcol™ line of alcohols marketed by Jarchem Industries, Inc. of Newark, N.J., including Jarcol™ I-18CG, I-20, I-12, I-16, I-18T, and 85BJ. In some cases, $R_2$ and $R_3$ may be sourced from certain alcohols to provide branched alkyls such as isostearyl and isopalmityl. It should be understood that such isopalmityl and isostearyl alkyl groups may cover any branched variation of $C_{16}$ and $C_{18}$, respectively. For example, the estolides described herein may comprise highly-branched isopalmityl or isostearyl groups at the $R_2$ and $R_3$ positions, derived from the Fineoxocol® line of isopalmityl and isostearyl alcohols marketed by Nissan Chemical America Corporation of Houston, Tex., including Fineoxocol® 180, 180N, and 1600. Without being bound to any particular theory, in certain embodiments, it is believed that introducing large, highly-branched alkyl groups (e.g., isopalmityl and isostearyl) at the $R_2$ or $R_3$ positions of the estolides can provide at least one way to increase the lubricant's viscosity, while substantially retaining or even reducing its pour point.

In some embodiments, the compounds described herein may comprise a mixture of two or more estolide compounds. It is possible to characterize the chemical makeup of an estolide, a mixture of estolides, or a composition comprising estolides by using the compound's, mixture's, or composition's, measured estolide number (EN). The EN of an estolide represents the average number of fatty acids added to the base fatty acid. The EN also represents the average number of estolide linkages per molecule. For example, with respect to Formula IV:

$$EN=n+1$$

wherein n is the number of secondary (β) fatty acids. Accordingly, a single estolide compound will have an EN that is a whole number, for example for dimers, trimers, and tetramers:

dimer EN=1
trimer EN=2
tetramer EN=3

However, a mixture of two or more estolide compounds may have an EN that is a whole number or a fraction of a whole number. For example, a mixture having a 1:1 molar ratio of dimer and trimer would have an EN of 1.5, while a mixture having a 1:1 molar ratio of tetramer and trimer would have an EN of 2.5.

As discussed above, in certain embodiments, the compounds of Formulas I/II and III represent subgenera of Formula IV. Thus, in some embodiments, a reference to the EN of a compound of Formulas I/II and III may be better understood when discussed in reference to Formula IV. By way of example, a compound of Formula I, when $R_2$ is selected from hydrogen and an alkyl group, may be described as being in its "dimer" form and having an EN of 1. That same compound can be described with reference to Formula IV, wherein m=2, n=0, and $R_4$ represents the group $Q^1(W^1)_q CH(W^2)_p CH(W^3)_z$—, such that EN=n+1=0+1=1. Similarly, by way of example, a compound of Formula I, when $R_2$ is a substituent of Formula II and n=1, may be described as being in its "tetramer" form and having an EN of 3. That same compound can be described with reference to Formula IV, wherein m=2, n=2, and $R_4$ represents the group $Q^3(W^6)_y CH(W^7)_x$—, such that EN=n+1=2+1=3. Similarly, compounds of Formula VI/II may be described with reference to Formula VII.

In some embodiments, the compositions may comprise a mixture of two or more estolides having an EN that is an integer or fraction of an integer that is greater than or equal to 1. In some embodiments, the EN may be an integer or fraction of an integer selected from about 1.0 to about 5.0. In some embodiments, the EN is an integer or fraction of an integer selected from 1.2 to about 4.5. In some embodiments, the estolide compounds described herein will be in there trimer form or larger, wherein the EN is greater than or equal to 2. Thus, in some embodiments, the EN is selected from an integer or fraction of an integer that is from about 2.0 to about 3.0, or from about 2.2 to about 2.8. In some embodiments, the EN is selected from a value greater than 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, and 5.0. In some embodiments, the EN is selected from a value less than 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, and 5.0.

As noted above, it should be understood that the chains of the estolide compounds may be independently optionally substituted, wherein one or more hydrogens are removed and replaced with one or more of the substituents identified herein. Similarly, two or more of the hydrogen residues may be removed to provide one or more sites of unsaturation, such as a cis or trans double bond. Further, the chains may optionally comprise branched hydrocarbon residues. In some embodiments the estolides described herein may comprise at least one compound of Formula IV:

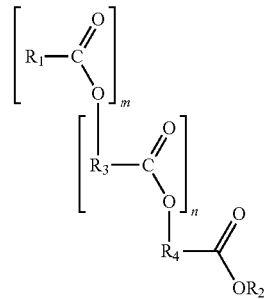

Formula IV wherein
n is equal to or greater than 0;
m is equal to or greater than 2;
$R_2$ is selected from hydrogen and optionally substituted alkyl that is saturated or unsaturated, and branched or unbranched; and
$R_1$, $R_3$ and $R_4$, independently for each occurrence, are selected from optionally substituted alkyl that is saturated or unsaturated, and branched or unbranched.

In some embodiments, m is an integer selected from 2, 3, 4, and 5. In some embodiments, n is an integer selected from 1, 2, 3, 4, 5, 6, 7, 8, 9, 10, 11, and 12. In some embodiments, one or more $R_3$ differs from one or more other $R_3$ in a compound of Formula IV. In some embodiments, one or more $R_3$ differs from $R_4$ in a compound of Formula IV. In some embodiments, if the compounds of Formula IV are prepared from one or more polyunsaturated fatty acids, it is possible that one or more of $R_3$ and $R_4$ will have one or more sites of unsaturation. In some embodiments, if the compounds of Formula IV are prepared from one or more branched fatty acids, it is possible that one or more of $R_3$ and $R_4$ will be branched.

Without being bound to any particular theory, in certain embodiments, altering the EN produces estolides having the desired viscometric properties while substantially retaining or even reducing pour point. For example, in some embodiments estolides exhibit a decreased pour point upon increasing the EN value. Accordingly, in certain embodiments, a method is provided for retaining or decreasing the pour point of an estolide base oil by increasing the EN of the base oil, or a method is provided for retaining or decreasing the pour point of a composition comprising an estolide base oil by increasing the EN of the base oil. In some embodiments, the method comprises: selecting an estolide base oil having an initial EN and an initial pour point; and removing at least a portion of the base oil, said portion exhibiting an EN that is less than the initial EN of the base oil, wherein the resulting estolide base oil exhibits an EN that is greater than the initial EN of the base oil, and a pour point that is equal to or lower than the initial pour point of the base oil. In some embodiments, the selected estolide base oil is prepared by oligomerizing at least one first unsaturated fatty acid with at least one second unsaturated fatty acid and/or saturated fatty acid. In some embodiments, the removing at least a portion of the base oil is accomplished by distillation, chromatography, membrane separation, phase separation, affinity separation, or combinations thereof. In some embodiments, the distillation takes place at a temperature and/or pressure that is suitable to separate the estolide base oil into different "cuts" that individually exhibit different EN values. In some embodiments, this may be accomplished by subjecting the base oil to a temperature of at least about 250° C. and an absolute pressure of no greater than about 25 microns. In some embodiments, the distillation takes place at a temperature range of about 250° C. to about 310° C. and an absolute pressure range of about 10 microns to about 25 microns.

Typically, base stocks and lubricant compositions exhibit certain lubricity, viscosity, and/or pour point characteristics. For example, in certain embodiments, suitable viscosity characteristics of the base oil may range from about 10 cSt to about 250 cSt at 40° C., and/or about 3 cSt to about 30 cSt at 100° C. In some embodiments, the estolide base stocks may exhibit viscosities within a range from about 50 cSt to about 150 cSt at 40° C., and/or about 10 cSt to about 20 cSt at 100° C.

In some embodiments, estolide compounds and compositions may exhibit viscosities less than about 55 cSt at 40° C. or less than about 45 cSt at 40° C., and/or less than about 12 cSt at 100° C. or less than about 10 cSt at 100° C. In some embodiments, estolide compounds and compositions may exhibit viscosities less than about 40 cSt at 40° C. or less than about 30 cSt at 40° C., and/or less than about 8 cSt at 100° C. or less than about 6 cSt at 100° C. In some embodiments, estolide compounds and compositions may exhibit viscosities less than about 20 cSt at 40° C., and/or less than about 5 cSt at 100° C. In some embodiments, estolide compounds and compositions may exhibit viscosities within a range from about 15 cSt to about 25 cSt at 40° C., and/or about 3 cSt to about 6 cSt at 100° C. In some embodiments, estolide compounds and compositions may exhibit viscosities within a range from about 18 cSt to about 20 cSt at 40° C., and/or about 4 cSt to about 5 cSt at 100° C. In some embodiments, the estolide compounds and compositions may exhibit viscosities of about 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, or 55 cSt at 40° C. In some embodiments, the estolide compounds and compositions may exhibit viscosities of about 1, 2, 3, 4, 5, 6, 7, 8, 9, 10, 11, 12, 13, 14, 15, 16, 17, 18, 19, 20, 25, or 30 cSt at 100° C.

In certain embodiments, estolides may exhibit desirable low-temperature pour point properties. In some embodiments, estolide compounds and compositions may exhibit a pour point lower than about −25° C., about −35° C., −40° C., or even about −50° C. In some embodiments, estolides have a pour point of about −25° C. to about −45° C. In some embodiments, the pour point falls within a range of about −30° C. to about −40° C., about −34° C. to about −38° C., about −30° C. to about −45° C., about −35° C. to about −45° C., 34° C. to about −42° C., about −38° C. to about −42° C., or about 36° C. to about −40° C. In some embodiments, the pour point falls within the range of about −27° C. to about −37° C., or about −30° C. to about −34° C. In some embodiments, the pour point falls within the range of about −25° C. to about −35° C., or about −28° C. to about −32° C. In some embodiments, the pour point falls within the range of about −28° C. to about −38° C., or about −31° C. to about −35° C. In some embodiments, the pour point falls within the range of about −31° C. to about −41° C., or about −34° C. to about −38° C. In some embodiments, the pour point falls within the range of about −40° C. to about −50° C., or about −42° C. to about −48° C. In some embodiments, the pour point falls within the range of about −50° C. to about −60° C., or about −52° C. to about −58° C. In some embodiments, the upper bound of the pour point is less than about −35° C., about −36° C., about −37° C., about −38° C., about −39° C., about −40° C., about −41° C., about −42° C., about −43° C., about −44° C., or about −45° C. In some embodiments, the lower bound of the pour point is greater than about −55° C., about −54° C., about −53° C., about −52° C., −51, about −50° C., about −49° C., about −48° C., about −47° C., about −46° C., or about −45° C.

In addition, in certain embodiments, estolides may exhibit decreased Iodine Values (IV) when compared to estolides prepared by other methods. IV is a measure of the degree of total unsaturation of an oil, and is determined by measuring the amount of iodine per gram of estolide (cg/g). In certain instances, oils having a higher degree of unsaturation may be more susceptible to creating corrosiveness and deposits, and may exhibit lower levels of oxidative stability. Compounds having a higher degree of unsaturation will have more points of unsaturation for iodine to react with, resulting in a higher IV. Thus, in certain embodiments, it may be desirable to reduce the IV of estolides in an effort to increase the oil's oxidative stability, while also decreasing harmful deposits and the corrosiveness of the oil.

In some embodiments, estolides described have an IV of less than about 40 cg/g or less than about 35 cg/g. In some embodiments, estolides will have an IV of less than about 30 cg/g, less than about 25 cg/g, less than about 20 cg/g, less than about 15 cg/g, less than about 10 cg/g, or less than about 5 cg/g. The IV of an estolide may be reduced by decreasing the estolide's degree of unsaturation. In certain embodiments, this may be accomplished by, for example, increasing the amount of saturated capping materials relative to unsaturated capping materials when synthesizing the estolides. Alternatively, in certain embodiments, IV may be reduced by hydrogenating estolides having unsaturated caps.

In some embodiments, estolides comprise at least one compound of Formula IV, wherein: n is 0; m is 2; $R_1$ for each occurrence is methyl; $R_4$ is selected from a saturated and unbranched $C_{17}$ alkyl; and $R_2$ is an optionally substituted $C_1$-$C_{40}$ alkyl that is saturated or unsaturated and branched or unbranched.

In some embodiments, estolides comprise at least one compound of Formula IV, wherein: n is 0; m is 3; $R_1$ for each occurrence is methyl; $R_4$ is selected from a saturated and unbranched $C_{17}$ alkyl; and $R_2$ is an optionally substituted $C_1$-$C_{40}$ alkyl that is saturated or unsaturated and branched or unbranched.

In some embodiments, estolides comprise at least one compound of Formula IV, wherein: n is 0; m is 2; $R_1$ for each occurrence is methyl; $R_4$ is selected from an unsaturated and unbranched $C_{17}$ alkyl; and $R_2$ is an optionally substituted $C_1$-$C_{40}$ alkyl that is saturated or unsaturated and branched or unbranched.

In some embodiments, estolides comprise at least one compound of Formula IV, wherein: n is 0; m is 2; $R_1$ for each occurrence is methyl; $R_4$ is selected from a saturated and unbranched $C_{17}$ alkyl; and $R_2$ is hydrogen.

In some embodiments, estolides comprise at least one compound of Formula IV, wherein: n is 0; m is 3; $R_1$ for each occurrence is methyl; $R_4$ is selected from a saturated and unbranched $C_{17}$ alkyl; and $R_2$ is hydrogen.

In some embodiments, estolides comprise at least one compound of Formula IV, wherein: n is 0; m is 2; $R_1$ for each occurrence is methyl; $R_4$ is selected from an unsaturated and unbranched $C_{17}$ alkyl; and $R_2$ is hydrogen.

The present disclosure further relates to methods of making estolides according to Formulas I-VII. By way of example, the reaction of a polyunsaturated fatty acid with an organic and/or fatty acid and the esterification of the resulting free acid estolide are illustrated and discussed below. Also are described methods of making epoxy estolides, and preparing poly-capped estolides from epoxy estolides.

As discussed in the schemes outlined further below, compound 102 represents a polyunsaturated fatty acid that may serve as the basis for preparing the poly-capped estolide compounds described herein.

Scheme 1

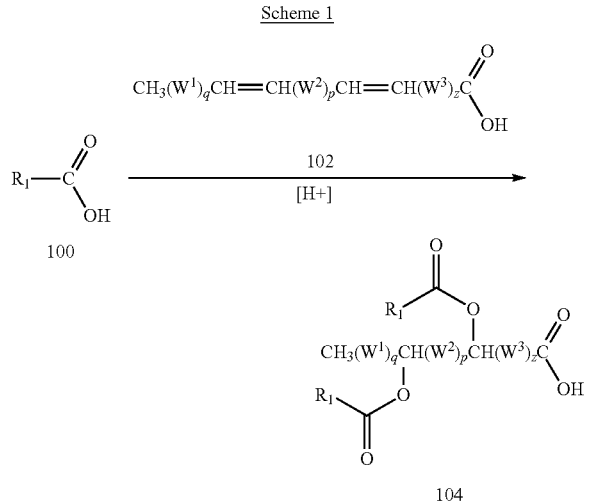

In Scheme 1, wherein $W^1$, $W^2$ and $W^3$ are independently selected from —$CH_2$— and —CH=CH—, and q, p and z are independently an integer selected from 0 to 15, polyunsaturated fatty acid 102 may be added to a solution containing an excess of carboxylic acid 100 and a proton from a proton source to form poly-capped free acid estolide 104. Carboxylic acid 100 may be any suitable organic acid (e.g., acetic acid) or fatty acid. In some embodiments, it may be desirable to use a saturated alkyl acid for carboxylic acid 100 ($R_1$=saturated alkyl group), as the use of one or more unsaturated fatty acids for carboxylic acid 100 may result in estolide formation prior to the addition of polyunsaturated fatty acid 102. The slow addition of polyunsaturated fatty acid 102 to an excess of carboxylic acid 100 (e.g., acetic acid) may help to maximize the addition of carboxylic acid 100 to the sites of unsaturation on polyunsaturated fatty acid 102, while minimizing the occurrence of inter-molecular linkages between two or more molecules of polyunsaturated acid 102. Any suitable proton source may be implemented to catalyze the formation of free acid estolide 104, including but not limited to homogenous acids and/or strong acids like hydrochloric acid, sulfuric acid, perchloric acid, nitric acid, triflic acid, and the like.

Scheme 2

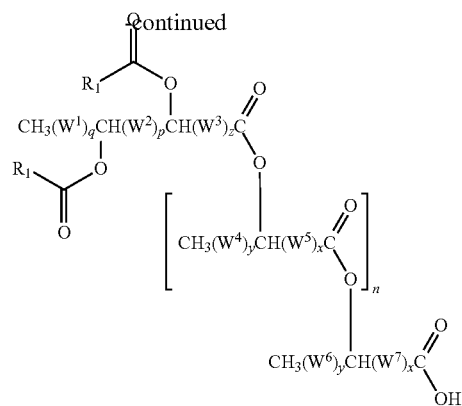

Alternatively, in Scheme 2, wherein $W^1$, $W^2$, $W^3$, $W^4$, $W^5$, $W^6$, and $W^7$ are independently selected from —$CH_2$— and —CH=CH—, q, p and z are independently an integer selected from 0 to 15, x and y, independently for each occurrence, are selected from 0 to 20, and n is an integer greater than or equal to 0, carboxylic acid 100 and a proton from a proton source may be added to polyunsaturated fatty acid 102 form free acid estolide 200. In certain embodiments, this may be desirable because starting with a solution of polyunsaturated fatty acid 100 under acidic conditions may help to increase oligomerization resulting from the inter-molecular linkage of two or more molecules of polyunsaturated acid 102. Subsequent addition of carboxylic acid 100, such as a saturated carboxylic acid (e.g., acetic acid), will provide poly-capped free acid estolide 200. To further increase oligomerization, it may be desirable to use an unsaturated fatty acid for carboxylic acid 100 ($R_1$=unsaturated alkyl group). Any suitable proton source may be implemented to catalyze the formation of free acid estolide 200, including but not limited to homogenous acids and/or strong acids like hydrochloric acid, sulfuric acid, perchloric acid, nitric acid, triflic acid, and the like.

Scheme 3

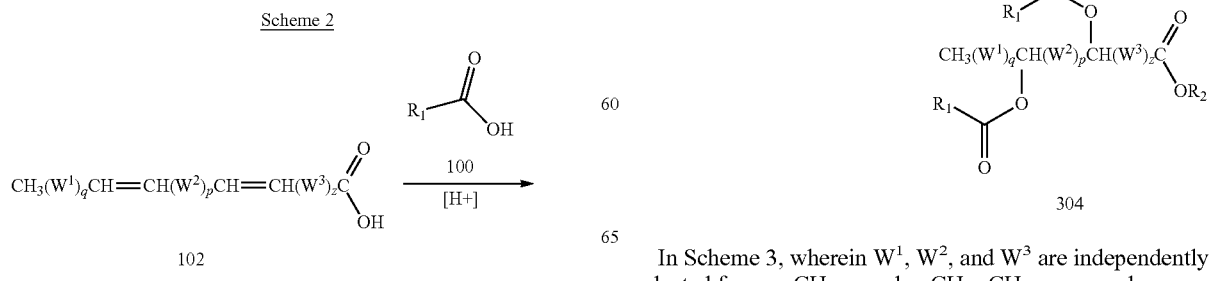

In Scheme 3, wherein $W^1$, $W^2$, and $W^3$ are independently selected from —$CH_2$— and —CH=CH—, q, p and z are independently an integer selected from 0 to 15, and $R_2$ is an optionally-substituted alkyl that is saturated or unsaturated, and branched or unbranched, poly-capped free acid estolide 104 may be esterified by any suitable procedure known to those of skilled in the art, such as acid-catalyzed reduction with alcohol 302, to yield esterified poly-capped estolide 304. This synthetic route may also be suitable for the esterification of free acid estolide 200. Other exemplary methods may include other types of Fischer esterification, such as those using Lewis acid catalysts such as $BF_3$.

Alternatively, poly-capped estolides may be prepared from monounsaturated fatty acids in accordance with the following schemes.

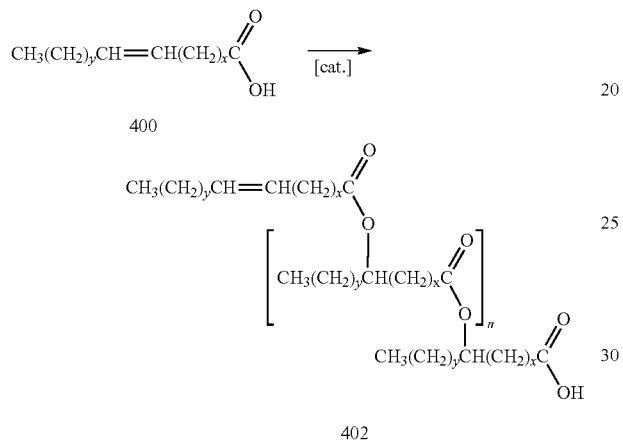

In Scheme 4, wherein x is, independently for each occurrence, an integer selected from 0 to 20, y is, independently for each occurrence, an integer selected from 0 to 20, and n is an integer greater than or equal to 0, unsaturated fatty acid 400 may be contacted with any catalyst suitable for effecting oligomerization, such as a proton from a proton source, to form free acid estolide 402. Suitable catalysts include but not limited to homogenous acids and/or strong acids like hydrochloric acid, sulfuric acid, perchloric acid, nitric acid, triflic acid, and the like.

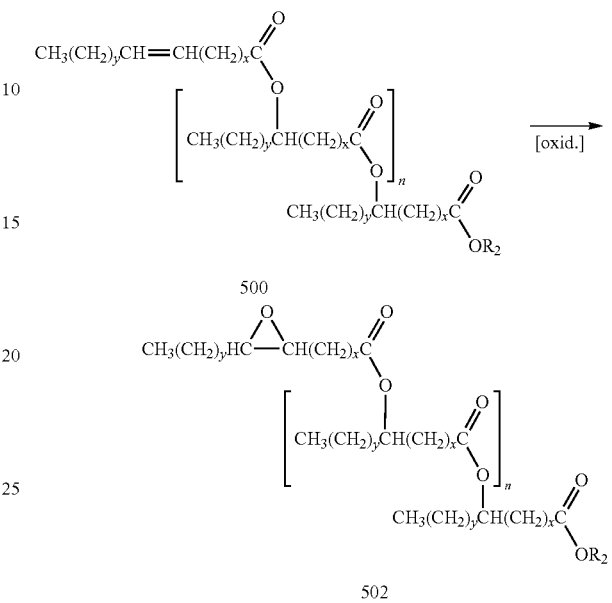

Starting with free-acid estolide 402, esterified estolide 500 may be prepared in a manner similar to the procedure set forth in Scheme 3. In Scheme 5, wherein x is, independently for each occurrence, an integer selected from 0 to 20, y is, independently for each occurrence, an integer selected from 0 to 20, $R_2$ is an optionally-substituted alkyl that is saturated or unsaturated, and branched or unbranched, and n is an integer greater than or equal to 0, esterified estolide 500 may be contacted with an oxidant suitable for effecting epoxidation, such as hydrogen peroxide and formic acid, to form epoxidized estolide 502.

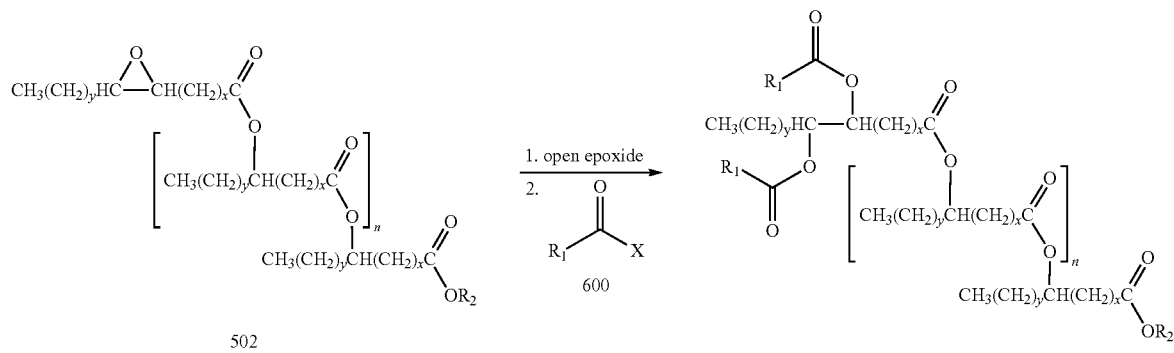

In Scheme 6, wherein x is, independently for each occurrence, an integer selected from 0 to 20, y is, independently for each occurrence, an integer selected from 0 to 20, n is an integer greater than or equal to 0, $R_2$ is an optionally-substituted alkyl that is saturated or unsaturated, and branched or unbranched, and $R_1$ is an optionally substituted alkyl group that is saturated or unsaturated, and branched or unbranched, epoxidized estolide 502 may be contacted with a compound or composition that will open the epoxide residue and provide the corresponding monohydroxy or dihydroxy variant, which may be isolated or generated in situ. For example, epoxidized estolide 502 may be contacted with an aqueous solution of acid, such as perchloric acid, to provide the dihydroxy estolide. Alternatively, epoxidized estolide 502 may be contacted with a fatty acid (such as octanoic acid) which will "cap" the estolide by reacting with the epoxide residue to provide the monohydroxy variant. Subsequently, the monohydroxy or dihydroxy estolide is contacted with electrophilic compound 600, where "x" is a leaving group (e.g., halide such as chlorine), to provide poly-capped estolide 602. In certain embodiments, electrophilic compound 600 is a fatty acid halide. Exemplary fatty acid halides include short-chain fatty acid chlorides such as hexanoyl and octanoyl chloride.

In certain embodiments, estolide compounds may meet or exceed one or more of the specifications for certain end-use applications, without the need for conventional additives. For example, in certain instances, high-viscosity lubricants, such as those exhibiting a kinematic viscosity of greater than about 120 cSt at 40° C., or even greater than about 200 cSt at 40° C., may be desirable for particular applications such as gearbox or wind turbine lubricants. Prior-known lubricants with such properties typically also demonstrate an increase in pour point as viscosity increases, such that prior lubricants may not be suitable for such applications in colder environments. However, in certain embodiments, the counterintuitive properties of certain compounds described herein (e.g., increased EN provides estolides with higher viscosities while retaining, or even decreasing, the oil's pour point) may make higher-viscosity estolides particularly suitable for such specialized applications.

Similarly, the use of prior-known lubricants in colder environments may generally result in an unwanted increase in a lubricant's viscosity. Thus, depending on the application, it may be desirable to use lower-viscosity oils at lower temperatures. In certain circumstances, low-viscosity oils may include those exhibiting a viscosity of lower than about 50 cSt at 40° C., or even about 40 cSt at 40° C. Accordingly, in certain embodiments, the low-viscosity estolides described herein may provide end users with a suitable alternative to high-viscosity lubricants for operation at lower temperatures.

In some embodiments, it may be desirable to prepare lubricant compositions comprising an estolide base stock. For example, in certain embodiments, the estolides described herein may be blended with one or more additives selected from polyalphaolefins, synthetic esters, polyalkylene glycols, mineral oils (Groups I, II, and III), pour point depressants, viscosity modifiers, anti-corrosives, antiwear agents, detergents, dispersants, colorants, antifoaming agents, and demulsifiers. In addition, or in the alternative, in certain embodiments, the estolides described herein may be co-blended with one or more synthetic or petroleum-based oils to achieve the desired viscosity and/or pour point profiles. In certain embodiments, the estolides described herein also mix well with gasoline, so that they may be useful as fuel components or additives.

In all of the foregoing examples, the compounds described may be useful alone, as mixtures, or in combination with other compounds, compositions, and/or materials.

Methods for obtaining the novel compounds described herein will be apparent to those of ordinary skill in the art, suitable procedures being described, for example, in the examples below, and in the references cited herein.

EXAMPLES

Analytics

Nuclear Magnetic Resonance:
NMR spectra were collected using a Bruker Avance 500 spectrometer with an absolute frequency of 500.113 MHz at 300 K using $CDCl_3$ as the solvent. Chemical shifts were reported as parts per million from tetramethylsilane. The formation of a secondary ester link between fatty acids, indicating the formation of estolide, was verified with $^1H$ NMR by a peak at about 4.84 ppm.

Estolide Number (EN):
The EN was measured by GC analysis. It should be understood that the EN of a composition specifically refers to EN characteristics of any estolide compounds present in the composition. Accordingly, an estolide composition having a particular EN may also comprise other components, such as natural or synthetic additives, other non-estolide base oils, fatty acid esters, e.g., triglycerides, and/or fatty acids, but the EN as used herein, unless otherwise indicated, refers to the value for the estolide fraction of the estolide composition.

Iodine Value (IV):
The iodine value is a measure of the degree of total unsaturation of an oil. IV is expressed in terms of centigrams of iodine absorbed per gram of oil sample. Therefore, the higher the iodine value of an oil the higher the level of unsaturation is of that oil. The IV may be measured and/or estimated by GC analysis. Where a composition includes unsaturated compounds other than estolides as set forth in Formula I-VII, the estolides can be separated from other unsaturated compounds present in the composition prior to measuring the iodine value of the constituent estolides. For example, if a composition includes unsaturated fatty acids or triglycerides comprising unsaturated fatty acids, these can be separated from the estolides present in the composition prior to measuring the iodine value for the one or more estolides.

Acid Value:
The acid value is a measure of the total acid present in an oil. Acid value may be determined by any suitable titration method known to those of ordinary skill in the art. For example, acid values may be determined by the amount of KOH that is required to neutralize a given sample of oil, and thus may be expressed in terms of mg KOH/g of oil.

Gas Chromatography (GC):
GC analysis was performed to evaluate the estolide number (EN) and iodine value (IV) of the estolides. This analysis was performed using an Agilent 6890N series gas chromatograph equipped with a flame-ionization detector and an autosampler/injector along with an SP-2380 30 m×0.25 mm i.d. column.

The parameters of the analysis were as follows: column flow at 1.0 mL/min with a helium head pressure of 14.99 psi; split ratio of 50:1; programmed ramp of 120-135° C. at 20° C./min, 135-265° C. at 7° C./min, hold for 5 min at 265° C.; injector and detector temperatures set at 250° C.

Measuring EN and IV by GC:
To perform these analyses, the fatty acid components of an estolide sample were reacted with MeOH to form fatty acid methyl esters by a method that left behind a hydroxy group at sites where estolide links were once present. Standards of fatty acid methyl esters were first analyzed to establish elution times.

Sample Preparation:

To prepare the samples, 10 mg of estolide was combined with 0.5 mL of 0.5M KOH/MeOH in a vial and heated at 100° C. for 1 hour. This was followed by the addition of 1.5 mL of 1.0 M $H_2SO_4$/MeOH and heated at 100° C. for 15 minutes and then allowed to cool to room temperature. One (1) mL of $H_2O$ and 1 mL of hexane were then added to the vial and the resulting liquid phases were mixed thoroughly. The layers were then allowed to phase separate for 1 minute. The bottom $H_2O$ layer was removed and discarded. A small amount of drying agent ($Na_2SO_4$ anhydrous) was then added to the organic layer after which the organic layer was then transferred to a 2 mL crimp cap vial and analyzed.

EN Calculation:

The EN is measured as the percent hydroxy fatty acids divided by the percent non-hydroxy fatty acids. As an example, a dimer estolide would result in half of the fatty acids containing a hydroxy functional group, with the other half lacking a hydroxyl functional group. Therefore, the EN would be 50% hydroxy fatty acids divided by 50% non-hydroxy fatty acids, resulting in an EN value of 1 that corresponds to the single estolide link between the capping fatty acid and base fatty acid of the dimer.

IV Calculation:

The iodine value is estimated by the following equation based on ASTM Method D97 (ASTM International, Conshohocken, Pa.):

$$IV = \Sigma \ 100 \times \frac{A_f \times MW_I \times db}{MW_f}$$

$A_f$=fraction of fatty compound in the sample
$MW_I$=253.81, atomic weight of two iodine atoms added to a double bond
db=number of double bonds on the fatty compound
$MW_f$=molecular weight of the fatty compound The properties of exemplary estolide compounds and compositions described herein are identified in the following examples and tables.

Other Measurements:

Except as otherwise described, pour point is measured by ASTM Method D97-96a, cloud point is measured by ASTM Method D2500, viscosity/kinematic viscosity is measured by ASTM Method D445-97, viscosity index is measured by ASTM Method D2270-93 (Reapproved 1998), specific gravity is measured by ASTM Method D4052, flash point is measured by ASTM Method D92, evaporative loss is measured by ASTM Method D5800, vapor pressure is measured by ASTM Method D5191, and acute aqueous toxicity is measured by Organization of Economic Cooperation and Development (OECD) 203.

Example 1

The acid catalyst reaction was conducted in a 50 gallon Pfaudler RT-Series glass-lined reactor. Oleic acid (65 Kg, OL 700, Twin Rivers) was added to the reactor with 70% perchloric acid (992.3 mL, Aldrich Cat #244252) and heated to 60° C. in vacuo (10 torr abs) for 24 hrs while continuously being agitated. After 24 hours the vacuum was released. 2-Ethylhexanol (29.97 Kg) was then added to the reactor and the vacuum was restored. The reaction was allowed to continue under the same conditions (60° C., 10 torr abs) for 4 more hours. At which time, KOH (645.58 g) was dissolved in 90% ethanol/water (5000 mL, 90% EtOH by volume) and added to the reactor to quench the acid. The solution was then allowed to cool for approximately 30 minutes. The contents of the reactor were then pumped through a 1 micron (μ) filter into an accumulator to filter out the salts. Water was then added to the accumulator to wash the oil. The two liquid phases were thoroughly mixed together for approximately 1 hour. The solution was then allowed to phase separate for approximately 30 minutes. The water layer was drained and disposed of. The organic layer was again pumped through a 1μ filter back into the reactor. The reactor was heated to 60° C. in vacuo (10 torr abs) until all ethanol and water ceased to distill from solution. The reactor was then heated to 100° C. in vacuo (10 torr abs) and that temperature was maintained until the 2-ethylhexanol ceased to distill from solution. The remaining material was then distilled using a Myers 15 Centrifugal Distillation still at 200° C. under an absolute pressure of approximately 12 microns (0.012 ton) to remove all monoester material leaving behind estolides (Ex. 1 estolides).

Example 2

The acid catalyst reaction is conducted in a 3-neck flask equipped with stir bar, thermometer, and distillation column. Whole cut coconut fatty acid (10 equiv., TRC 110, Twin Rivers) are added to the flask with 70% perchloric acid (0.05 equiv., Aldrich Cat #244252) and heated to 60° C. in vacuo (10 torr abs) while continuously being agitated. Linoleic acid (1 equiv., Aldrich Cat # L1376) is added dropwise by syringe pump over a period of about 12-18 hours. Heating the vessel under reduced pressure is continued for a total of about 24 hours, after which the vacuum is released. At which time, the acid catalyst is quenched with a molar equivalent of KOH dissolved in 90% ethanol in water for 30 min under continuous agitation. The solution is then allowed to cool for approximately 30 minutes. The contents of the flask are then pumped through a 1 micron (μ) filter into an accumulator to filter out the salts. Water is then added to the accumulator to wash the oil. The two liquid phases are thoroughly mixed together for approximately 1 hour. The solution is then allowed to phase separate for approximately 30 minutes. The water layer is drained and disposed of. The organic layer is again pumped through a 1μ filter back into the flask. The reactor is heated to 60° C. in vacuo (10 torr abs) until all ethanol and water ceased to distill from solution. Single-capped estolides (one α-chain) are then separated from poly-capped estolides (two α-chains) and unreacted fatty acids using any suitable methods known to those of skill in the art, such as distillation or chromatography.

Example 3

The poly-capped estolide product of Example 2 is placed in a round bottom flask equipped with a stir bar and a solution of $BF_3.OEt_2$ (0.15 equiv.) and 2-ethylhexanol (1.2 equiv.) The solution is then heated to 60° C. under stirring for 3-4 hours. The reaction mixture is then cooled to room temperature and quenched with water. The oil is separated and washed with brine followed by drying over sodium sulfate. The esterified product is recovered from any unreacted 2-ethylhexanol using any suitable methods known to those of skill in the art, such as distillation or chromatography.

Example 4

The syntheses set forth in Examples 2 and 3 are repeated, except linoleic acid is substituted with α-linolenic acid (1 equiv., Aldrich Cat # L2378) to provide free acid estolides and esterified estolides capped with one, two and three fatty acid residues.

Example 5

The syntheses set forth in Examples 2-4 are repeated, except the whole cut coconut fatty acids are substituted with acetic acid (10 equiv., Aldrich Cat #320099) to provide free acid estolides and esterified estolides capped with one, two, and three acetic acid residues.

Example 6

Estolides produced according to the method set forth in Example 1 (Ex. 1) were subjected to distillation conditions in a Myers 15 Centrifugal Distillation still at 300° C. under an absolute pressure of approximately 12 microns (0.012 torr). This resulted in a primary distillate having a lower EN average (Ex. 6A), and a distillation residue having a higher EN average (Ex. 6B). Certain data are reported below in Table 1.

TABLE 1

| Estolide Base Stock | EN | Pour Point (° C.) | Iodine Value (cg/g) |
|---|---|---|---|
| Ex. 6A | 1.35 | −32 | 31.5 |
| Ex. 1 | 2.34 | −40 | 22.4 |
| Ex. 6B | 4.43 | −40 | 13.8 |

Example 7

Estolides were made according to the method set forth in Example 1, and processed according to the distillation conditions of Example 6 to provide estolides of Ex. 6A and 6B. Ex. 6A estolides (1.0 eq.) were added to a round bottom flask, cooled to 5° C., along with aqueous $H_2O_2$ (4 eq.) and formic acid (4.1 eq.). The mixture was stirred vigorously and allowed to warm to room temperature. Stirring of the reaction mixture was allowed to continue for a total of 72 hours. The reaction mixture was then extracted in a separatory funnel with hexanes and washed with an aqueous sodium sulfite solution. The organic layer was washed several more times with deionized water and dried over magnesium sulfate (anhydrous), and filtered. The solvents were then removed in a rotary evaporator to yield epoxidized estolides (Ex. 7 epoxy estolides).

Example 8

Epoxidized estolides were prepared according to the method set forth in Example 7. Ex. 7 epoxy estolides (1 equiv.) were reacted with octanoic acid (4 equiv.) at 100° C. for 6 hrs. Excess octanoic acid was removed via distillation under reduced pressure and the resulting mono-octanoate was treated with octanoyl chloride (1.4 equiv.) and triethylamine (1.4 equiv.) in dichloromethane at room temperature and the reaction stirred for 12 hrs. The crude reaction mixture was worked up with aqueous sodium bicarbonate, dried with sodium sulfate, and concentrated to provide poly-capped estolides (Ex. 8 poly-capped product) that include the following isomers:

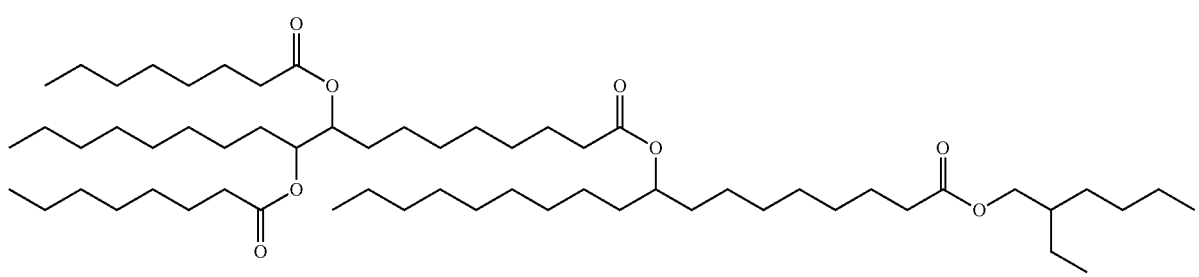

Isomer A

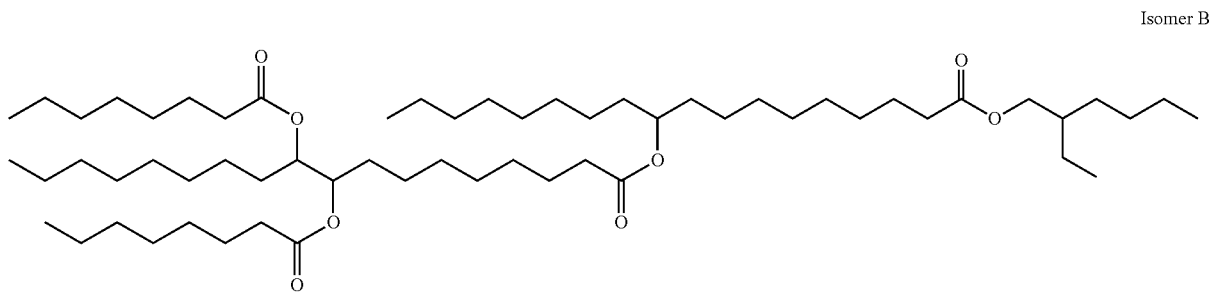

Isomer B

TABLE 2

|  | Visc. @ 40° C. | Visc. @ 100° C. | Visc. Index | Pour Point | Cloud point |
|---|---|---|---|---|---|
| Ex. 8 poly-capped product | 69.6 cSt | 11.8 cSt | 166 | −33° C. | −25° C. |

Example 9

Estolides are prepared according to the methods set forth in Examples 1-8, except the 2-ethylhexanol esterifying alcohol is replaced with various alcohols, including those identified below.

TABLE 3

| Alcohol | Structure |
|---|---|
| Jarcol ™ I-18CG | iso-octadecanol |
| Jarcol ™ I-12 | 2-butyloctanol |
| Jarcol ™ I-20 | 2-octyldodecanol |
| Jarcol ™ I-16 | 2-hexyldecanol |
| Jarcol ™ 85BJ | cis-9-octadecen-1-ol |
| Fineoxocol ® 180 | (branched structure) |
| Jarcol ™ I-18T | 2-octyldecanol |

Example 10

Estolides are prepared according to the methods set forth in Examples 1-8, except the 2-ethylhexanol esterifying alcohol is replaced with various alcohols, including those set forth below, which may be saturated or unsaturated and unbranched or substituted with one or more alkyl groups selected from methyl, ethyl, propyl, isopropyl, butyl, isobutyl, sec-butyl, tert-butyl, pentyl, isopentyl, neopentyl, hexyl, isohexyl, and the like, to form a branched residue at the $R_2$ position:

TABLE 4

| Alcohol | $R_2$ Substituents |
|---|---|
| $C_1$ alkanol | methyl |
| $C_2$ alkanol | ethyl |
| $C_3$ alkanol | n-propyl, isopropyl |
| $C_4$ alkanol | n-butyl, isobutyl, sec-butyl |
| $C_5$ alkanol | n-pentyl, isopentyl neopentyl |
| $C_6$ alkanol | n-hexyl, 2-methyl pentyl, 3-methyl pentyl, 2,2-dimethyl butyl, 2,3-dimethyl butyl |
| $C_7$ alkanol | n-heptyl and other structural isomers |
| $C_8$ alkanol | n-octyl and other structural isomers |
| $C_9$ alkanol | n-nonyl and other structural isomers |
| $C_{10}$ alkanol | n-decanyl and other structural isomers |
| $C_{11}$ alkanol | n-undecanyl and other structural isomers |
| $C_{12}$ alkanol | n-dodecanyl and other structural isomers |
| $C_{13}$ alkanol | n-tridecanyl and other structural isomers |
| $C_{14}$ alkanol | n-tetradecanyl and other structural isomers |
| $C_{15}$ alkanol | n-pentadecanyl and other structural isomers |
| $C_{16}$ alkanol | n-hexadecanyl and other structural isomers |
| $C_{17}$ alkanol | n-heptadecanyl and other structural isomers |
| $C_{18}$ alkanol | n-octadecanyl and other structural isomers |
| $C_{19}$ alkanol | n-nonadecanyl and other structural isomers |
| $C_{20}$ alkanol | n-icosanyl and other structural isomers |
| $C_{21}$ alkanol | n-heneicosanyl and other structural isomers |
| $C_{22}$ alkanol | n-docosanyl and other structural isomers |

Example 11

"Ready" and "ultimate" biodegradability of the estolide produced in Ex. 1 was tested according to standard OECD procedures. Results of the OECD biodegradability studies are set forth below:

TABLE 5

|  | 301D 28-Day (% degraded) | 302D Assay (% degraded) |
|---|---|---|
| Canola Oil | 86.9 | 78.9 |
| Ex. 1 Base Stock | 64.0 | 70.9 |

The Ex. 1 estolide base stock was tested under OECD 203 for Acute Aquatic Toxicity. The tests showed that the estolides are nontoxic, as no deaths were reported for concentration ranges of 5,000 mg/L and 50,000 mg/L.

The invention claimed is:

1. A method of preparing an estolide compound, comprising
   selecting an epoxidized estolide having at least one epoxy residue; and
   opening the at least one epoxy residue to provide an estolide compound having at least one hydroxy residue.

2. The method according to claim 1, further comprising acylating the at least one hydroxy residue with at least one acylating agent.

3. The method according to claim 2, wherein the at least one acylating agent is a fatty acid halide.

4. The method according to claim 1, wherein the epoxidized estolide is prepared by contacting an unsaturated estolide compound having at least one site of unsaturation with an epoxidizing agent.

5. The method according to claim 4, wherein the epoxidizing agent is selected from at least one of a peroxide or a percarboxylic acid.

6. The method according to claim 1, wherein opening the at least one epoxy residue comprises contacting the epoxidized estolide with at least one alcohol or at least one fatty acid.

7. The method according to claim 1, wherein the estolide compound comprises at least one compound according to Formula VI:

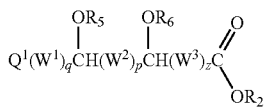

Formula VI wherein
z is an integer selected from 0 to 15;
p is an integer selected from 0 to 15;
q is an integer selected from 0 to 15;
$R_5$ and $R_6$ are independently selected from hydrogen, —C(O)$R_1$, and an optionally substituted alkyl that is saturated or unsaturated, and branched or unbranched;
$R_1$, independently for each occurrence, is selected from optionally substituted alkyl that is saturated or unsaturated, and branched or unbranched; and
$R_2$ is selected from a substituent represented by Formula II:

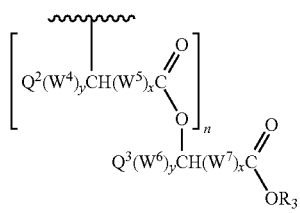

Formula II wherein
x is, independently for each occurrence, an integer selected from 0 to 20;
y is, independently for each occurrence, an integer selected from 0 to 20;
n is 0 or greater than 0;
$R_3$ is selected from hydrogen and optionally substituted alkyl that is saturated or unsaturated, and branched or unbranched;
$W^1$, $W^2$, $W^3$, $W^4$, $W^5$, $W^6$, and $W^7$, independently for each occurrence, are selected from —$CH_2$— and —CH=CH—; and
$Q^1$, $Q^2$, and $Q^3$, independently for each occurrence, are selected from hydrogen and —$CH_3$,
wherein each fatty acid chain residue of said at least one compound is independently optionally substituted.

8. The method according to claim 7, wherein $R_5$ and $R_6$ are independently selected from hydrogen and —C(O)$R_1$.

9. The method according to claim 8, wherein $R_1$, independently for each occurrence, is selected from optionally substituted $C_1$ to $C_{18}$ alkyl that is saturated or unsaturated, and branched or unbranched.

10. The method according to claim 8, wherein $R_1$, independently for each occurrence, is selected from $C_5$ to $C_{11}$ alkyl.

11. The method according to claim 9, wherein $R_1$ is saturated and unbranched for each occurrence.

12. The method according to claim 7, wherein $R_5$ and $R_6$ are hydrogen.

13. The method according to claim 7, wherein $R_5$ and $R_6$ are independently selected from hydrogen and optionally substituted alkyl that is saturated or unsaturated, and branched or unbranched.

14. The method according to claim 13, wherein $R_5$ and $R_6$ are independently selected from hydrogen and $C_1$-$C_{10}$ alkyl.

15. The method according to claim 7, wherein $W^1$, $W^2$, $W^3$, $W^4$, $W^5$, $W^6$ and $W^7$ for each occurrence are —$CH_2$—.

16. The method according to claim 7, wherein
x is, independently for each occurrence, an integer selected from 0 to 10;
y is, independently for each occurrence, an integer selected from 0 to 10; and
n is an integer selected from 0 to 8,
wherein each fatty acid chain residue is unsubstituted.

17. The method according to claim 16, wherein x+y is, independently for each fatty acid chain residue, an integer selected from 13 to 15.

18. The method according to claim 17, wherein x+y is 15 for one or more fatty acid chain residues.

19. The method according to claim 7, wherein z is an integer selected from 0 to 12.

20. The method according to claim 19, wherein z is 7.

21. The method according to claim 17, wherein p is an integer selected from 0 to 6.

22. The method according to claim 21, wherein p is an integer selected from 1, 2 and 3.

23. The method according to claim 21, wherein p is 0.

24. The method according to claim 7, wherein q is an integer selected from 0 to 8.

25. The method according to claim 24, wherein q is 7.

26. The method according to claim 24, wherein q is 0.

27. The method according to claim 24, wherein q is an integer selected from 5 and 6.

28. The method according to claim 24, wherein q is an integer selected from 2 and 3.

29. The method according to claim 7, wherein z+p+q is an integer selected from 12 to 20.

30. The method according to claim 29, wherein z+p+q is 14 or 15.

31. The method according to claim 7, wherein z+p+q is 7.

32. The method according to claim 7, wherein $R_3$ is selected from optionally substituted $C_1$ to $C_{20}$ alkyl that is saturated or unsaturated and branched or unbranched.

33. The method according to claim 32, wherein $R_3$ is selected from methyl, ethyl, propyl, butyl, pentyl, hexyl, heptyl, octyl, nonyl, decanyl, undecanyl, dodecanyl, tridecanyl, tetradecanyl, pentadecanyl, hexadecanyl, heptadecanyl, octadecanyl, nonadecanyl, and icosanyl, which are saturated or unsaturated and branched or unbranched.

34. The method according to claim 7, wherein $R_3$ is hydrogen.

35. The method according to claim 7, wherein $Q^1$ is hydrogen.

36. The method according to claim 7, wherein $Q^1$, $Q^2$, and $Q^3$ are hydrogen.

37. The method according to claim 36, wherein q is 0.

* * * * *